(12) United States Patent
Kaner

(10) Patent No.: US 10,406,019 B1
(45) Date of Patent: Sep. 10, 2019

(54) SLEEP APNEA DEVICE AND KIT

(71) Applicant: Albert H. Kaner, Playa Vista, CA (US)

(72) Inventor: Albert H. Kaner, Playa Vista, CA (US)

(*) Notice: Subject to any disclaimer, the term of this patent is extended or adjusted under 35 U.S.C. 154(b) by 0 days.

(21) Appl. No.: 16/440,653

(22) Filed: Jun. 13, 2019

Related U.S. Application Data

(63) Continuation-in-part of application No. 16/125,704, filed on Sep. 9, 2018, which is a continuation of application No. 14/181,432, filed on Feb. 14, 2014, now abandoned.

(51) Int. Cl.
| | | |
|---|---|---|
| *A61F 5/56* | (2006.01) | |
| *A61M 16/04* | (2006.01) | |
| *A61C 7/08* | (2006.01) | |

(52) U.S. Cl.
CPC ............ *A61F 5/566* (2013.01); *A61C 7/08* (2013.01); *A61F 2005/563* (2013.01); *A61M 16/0488* (2013.01); *A61M 16/0495* (2014.02)

(58) Field of Classification Search
CPC .... A61F 5/56; A61F 5/566; A61F 5/58; A61F 5/0006; A61F 2005/563; A61F 2/20; A61B 13/00; A61B 2071/086; A61B 2071/088; A61C 7/00; A61C 7/08; A61C 7/10; A61C 7/145; A61C 5/80; A61C 5/82; A61C 5/90; A63B 71/085; A61M 16/0488; A61M 16/049; A61M 16/0493; A61M 16/0495; A61M 16/0497
USPC ....... 128/848, 859–863; 602/902; 433/6, 19, 433/93, 140; 600/239–240
See application file for complete search history.

(56) References Cited

U.S. PATENT DOCUMENTS

| | | | |
|---|---|---|---|
| 4,901,737 A | | 2/1990 | Toone |
| 5,007,828 A | * | 4/1991 | Rosenberg ............... A61C 7/00 433/17 |
| 5,915,385 A | | 6/1999 | Hakimi |
| 7,533,674 B2 | | 5/2009 | Dort |
| 7,607,439 B2 | | 10/2009 | Li |
| 8,028,705 B2 | | 10/2011 | Li |
| 2002/0144685 A1 | | 10/2002 | Ivanovich et al. |
| 2004/0045555 A1 | | 3/2004 | Nelson et al. |

(Continued)

FOREIGN PATENT DOCUMENTS

DE        19503288 C1       7/1996

*Primary Examiner* — Alireza Nia
*Assistant Examiner* — Rachel A Berezik
(74) *Attorney, Agent, or Firm* — Loza & Loza, LLP; Heidi L. Eisenhut

(57) ABSTRACT

A sleep apnea device includes a bite block, a plurality of receivers coupled to a lingual surface of the bite block, a plurality of transition pieces corresponding to the plurality of receivers. Each transition piece may include a vertical portion coupled to a corresponding receiver of the plurality of receivers, a horizontal portion configured to extend from the vertical portion, and a dam securing member fixed to one of the vertical portion, the horizontal portion, or both the vertical portion and the horizontal portion. The device may also include a plurality of base connectors corresponding to the plurality of transition pieces, a base coupled to the plurality of base connectors, and a resilient dam configured to be releasably secured by each dam securing member of the plurality of transition pieces. A kit including the sleep apnea device is also disclosed.

18 Claims, 13 Drawing Sheets

(56) References Cited

U.S. PATENT DOCUMENTS

| | | |
|---|---|---|
| 2004/0045556 A1 | 3/2004 | Nelson et al. |
| 2004/0049102 A1 | 3/2004 | Nelson et al. |
| 2006/0005843 A9 | 1/2006 | Nelson et al. |
| 2007/0289600 A1 | 12/2007 | Li |
| 2010/0139666 A1 | 6/2010 | Bonnaure |
| 2012/0031410 A1 | 2/2012 | Jackson |
| 2012/0138071 A1 | 6/2012 | Summer |
| 2012/0247485 A1 | 10/2012 | Timmons |
| 2014/0190490 A1 * | 7/2014 | Walker .................... A61F 5/566 128/848 |

* cited by examiner

SLEEP APNEA DEVICE AND KIT

CROSS-REFERENCE TO RELATED APPLICATION

This application is a continuation-in-part of U.S. patent application Ser. No. 16/125,704, filed Sep. 9, 2018, which is a continuation of U.S. patent application Ser. No. 14/181,432 filed Feb. 14, 2014, the contents of each are incorporated by reference herein.

BACKGROUND

Technical Field

The present disclosure relates to an apparatus and a kit relating to sleep apnea and, in particular, to improvements in such apparatus and kits in which a tongue or a patient is prevented from sliding (or falling backward) into an airway of the patient during sleep, by restricting the tongue's ability to do so, but not to impede otherwise movement of the tongue, that is, to permit the tongue to move freely as normal, with the exception of its sliding (or falling backward), so as to enable as little disturbance to the patient's sleep.

INTRODUCTION

Sleep apnea happens when the uvula and/or the tongue go limp and fall backward, blocking the airway, preventing oxygenation for the brain, heart and other organs. The patient never achieves a rapid eye movement (REM) state sleep and wakes up tired, not rested.

Sleep apnea is a major problem affecting both genders and all ages. There are several forms of sleep apnea, the main type, which most people have, is called "obstructive sleep apnea-OSA." This type of sleep apnea means that the patients stop breathing at night at different intervals because the tongue becomes soft and flaccid, raises up and falls backward blocking the airway. To be certain of the proper diagnosis, the patient must seek a physician trained in sleep apnea, who has the patient sleep overnight in a comfortable setting where they are hooked up with wires to determine all of the things necessary to make a correct diagnosis, that the patient, indeed, has the problem of sleep apnea. If that is the case, there will be periods of time where the patient will stop breathing, diminishing his oxygen intake, vital to brain and other tissue functioning.

Sleep apnea devices described herein may be contrasted to external devices made by physicians, i.e. bi-pap and c-pap machines.

According to some examples, a mandibular bite block made by a dentist, fits over the lower jaw (like mouth guard). Components couple to the mandibular bite block including, for example, a protective cover and five frames, which each may include a horizontal piece, which has a fastener that couples (for example, by a rivet) to an elliptical cover that is coupled to the five frames. The five frames may be the same or similar. The horizontal part slides horizontally and ends in a vertical part, which slides into a cylinder attached to the mandibular bite block giving it vertical movement. Each of the five frames fits into its own cylinder attached to the mandibular bite block.

The manufacturer makes the device of any suitable material, for example, a nontoxic, FDA approved, soft, elastic plastic known for its light weight and a harder plastic where necessary. The bite block may be constructed by the dentist and the five cylinders are attached in the appropriate positions to the bite block. The prefabricated device may be inserted into the bite-block cylinders. Once in place, the device's dam, made of a soft resilient plastic, latex, nitrile, rubber, or rubber-like material, lies on the tongue of the patient, holding it flat, unable to rise up and back to block the airway.

This device changes its dimensions automatically to accommodate all size jaws, long and short, wide and narrow. It does this by movement of the parts shown in, for example, FIG. 3A and FIG. 3B, for wider, or narrower jaws, the back and forth movement is invoked. For longer or shorter jaws, the devices parts are positioned in the appropriate positions and do the same movement for length of jaw, rather than width.

In some examples, the soft resilient plastic, latex, nitrile, rubber, or rubber-like material may be used to constrain the tongue, allowing the tongue to move while sleeping and not prevent sleep, since the body requires it for a restful slumber.

Sleep Apnea is known as a silent killer unless you are diagnosed and know that you have this problem, you cannot treat it, and bring it under control. Each year, around 38,000 cardiovascular deaths are attributed to obstructive sleep apnea (OSA).

Sleep Apnea is caused by the lack of oxygen for the body which our bodies so desperately need to sustain life, for our hearts, brain, blood and all of our tissues. No one is immune from this need, young, old, male or female.

When we sleep, the soft tissue in our mouth becomes limp, flaccid, the top of the tongues raises up, and becomes vertical and blocks the airway in our mouth, depriving us of our much needed supply of precious oxygen which is needed for air which gives us our needed oxygen, so that when we awaken, we are more tired than when we went to sleep since we require deep slumber to achieve the REM sleep. When we don't get it, we awaken, more tired than when retired. When we don't get that, we are not alert which is why there are so many auto accidents—fender benders—we cause damage to ourselves and others.

When we display unusual habits, such as snoring, we owe it to ourselves, and others to get diagnosed to see whether or not we have the problem of sleep apnea. There are different doctors who treat this problem and use different devices. Thus, there is an academy of sleep apnea comprised of MDs and DDSs, physicians and dentists, Medical Doctors and Doctors of Dental Surgery.

The MDs tread their sleep apnea patients with extra oral (outside the mouth) devices such as BI-PAP and C-PAP and the dentists treat this problem with intra oral devices such as mouth guards, which many people use while playing sports to protect their mouth and teeth from being injured. Most people prefer the oral devices which they feel is a superior option, sue tot eh factor of "compliance". What this means is that for the device to work successfully for this dangerous problem, people must use the treatment all of the time, not occasionally. It doesn't work if you don't use it.

Why people don't treat this disease constantly is that the extra oral devices are so difficult to use, ugly and difficult to clean, long tubing, difficult to clean off the bacteria from the inner part of the tubing, which is used to breath in the oxygen with the face mask.

The sleep apnea devices described herein work differently and are by contrast easy and relatively inexpensive to clean. Just put the mouth guard into a denture cleaning and within minutes it is cleaned and ready to use. The inventor has sleep apnea and is aware of the difficulties surrounding the condition and has been devoted to doing something about it.

Disclosed herein is a simple device which automatically fits all size jaws (lower), does not harm patients, and is easy to clean.

Known apparatus and methods physically hold the tongue captive, e.g., by using a vacuum or a tongue tip holder device that holds the tip of the tongue, rendering the tongue immobile. Adjustment of the position of lower jaw or locking the tongue into position in any fashion undesirable. Tampering with the temporomandibular joint (TMJ), changing position of the lower jaw by moving the lower jaw forward and/or opening the bite unnecessarily changes the anatomic orientation of the mouth during sleep. Locking the tongue into position by action of suction or by otherwise holding the tip of the tongue, is at least uncomfortable and possibly harmful to a person. A person's sleep may be undesirably interrupted (or prevented) when the tongue is prevented from moving normally during sleep.

Some further concerns may occur in prior art continuous positive airway pressure (CPAP) and Bilevel Positive Airway Pressure (BiPAP or BPAP) apparatus, that employ masks that are coupled to air-pumping machines and in which, by providing air for the airway, several problems can arise from their use, such as the formation of cancer or mold due to the difficulty of their being able to be cleaned. Additionally, nasal bubbles may form within a mask of a CPAP or BiPAP device, and it may be difficult to balance proper pressure for keeping nasal bubbles in position to provide an adequate airway to the patient, and the equipment used is not well designed to allow proper cleaning. The tongue may still be blocked if not physically held and prevented from occluding the airway. In addition, such apparatus is unattractive, perhaps even frightening, and to be at least an impediment to conversation.

BRIEF SUMMARY OF SOME EXAMPLES

The following presents a simplified summary of some aspects to provide a basic understanding of such aspects. This summary is not an extensive overview of all contemplated features of the disclosure and is intended neither to identify key or critical elements of all aspects nor to delineate the scope of any or all aspects. Its sole purpose is to present various concepts of some aspects in a simplified form as a prelude to the more detailed description that is presented later.

According to some aspects, a sleep apnea device may include a bite block configured to be releasably secured to lower teeth of a patient. A plurality of receivers may be coupled to a lingual surface of the bite block. The sleep apnea device may also include a plurality of transition pieces corresponding to the plurality of receivers. Each of the transition pieces may have a vertical portion coupled to a corresponding receiver of the plurality of receivers, a horizontal portion configured to extend from the vertical portion. According to some aspects, the horizontal portion may extend from the vertical portion, and, using various exemplary descriptions, may extend from the vertical portion toward an interior of an oral cavity of a patient, toward an interior of a mouth of a patient, toward a tongue of the patient. Each transition piece may also include a dam securing member fixed to one of the vertical portion, the horizontal portion, or both the vertical portion and the horizontal portion. The sleep apnea device may further include a plurality of base connectors corresponding to the plurality of transition pieces, each of the plurality of base connectors coupled to the horizontal portion of a corresponding one of the plurality of transition pieces and configured to slide, with respect to the horizontal portion, toward and away from the vertical portion. The sleep apnea device may also include a base coupled to the plurality of base connectors and a resilient dam configured to be releasably secured by each dam securing member of the plurality of transition pieces.

The bite block may fit over the lower teeth so that the entire sleep apnea device articulates with respect to upper teeth of an upper jaw of the patient. In some examples, the plurality of receivers may be coupled to the lingual surface of the bite block by being formed as one unit with the bite block. In other examples, the plurality of receivers is coupled to the lingual surface of the bite block using at least one of: a bonding agent, an epoxy, a cement, or a glue.

According to some aspects, the vertical portion of a transition piece may be coupled to the corresponding receiver by slidably engaging with a receiving portion of the corresponding receiver. In some examples, a detent mechanism may be formed by a first feature of the vertical portion of each transition piece engaged with a second feature of the corresponding receiver, and the detent mechanism may be configured to provide a stepped vertical translation of each transition piece with respect to the corresponding receiver and to provide a predefined angular rotation of each transition piece with respect to the corresponding receiver. The predefined angular rotation may be greater than or equal to about ±10 degrees and less than or equal to about ±45 degrees with respect to a central vertical axis of the corresponding receiver.

In some examples, the resilient dam may be configured to allow the tongue to slidably move against the resilient dam and prevent the tongue from sliding into an airway of the patient.

The sleep apnea device may also include a cover coupled to the base. The cover may have a top side and a bottom side, and the cover may be configured to be coupled to the base using a third fastener, fixed to or integral with the bottom side of the cover, that couples to a fourth fastener, fixed to or integral with a top side of the base. The cover may have a top side and a bottom side and the cover may be configured to be coupled to the base using a plurality of fasteners, fixed to or integral with the bottom side of the cover, that couple to a corresponding plurality of mating fasteners, each of the plurality of mating fasteners fixed to or integral with a top side of a corresponding base connector.

A coordinate system having an x-axis, a y-axis, and a z-axis, may be described with reference to the sleep apnea device and/or any component, part, or piece of it. In such examples, the base may be configured to translate along the x-axis, translate along the y-axis, and rotate about the z-axis in response to movements of the tongue influencing a position of the base. In other examples, a translation of each of the plurality of transition pieces along the z-axis may be selectively fixed in predetermined stepped increments.

In some aspects, the resilient dam may include a peripheral member on a circumference of the resilient dam and the peripheral member may be configured to be releasably secured by each dam securing member of the plurality of transition pieces.

In aspects where the resilient dam is included in a resilient dam structure, the resilient dam structure may include the resilient dam, a peripheral member on a circumference of the resilient dam, and a plurality of attachment features distributed around the peripheral member. The plurality of attachment features may be configured to be releasably secured by and/or to each dam securing member of the plurality of transition pieces.

According to some examples, the bite block may be configured to be releasably secured to lower teeth of the patient with a plurality of clasps, each of the plurality of clasps may have a first end configured to be secured to one or more of the lower teeth of the patient and a second end, distal to the first end, configured to be releasably secured to the bite block.

A kit for a sleep apnea device, may include a bite block configured to be releasably secured to lower teeth of a patient, a plurality of receivers configured to be coupled to a lingual surface of the bite block, a plurality of transition pieces corresponding to the plurality of receivers. In the kit, each transition piece of the plurality of transition pieces may include a vertical portion configured to be coupled to a corresponding receiver of the plurality of receivers, a horizontal portion configured to extend from the vertical portion. According to some aspects, the horizontal portion may extend from the vertical portion, and, using various exemplary descriptions, may extend from the vertical portion toward an interior of an oral cavity of a patient, toward an interior of a mouth of a patient, toward a tongue of the patient. Each transition piece may also include a dam securing member fixed to one of the vertical portion, the horizontal portion, or both the vertical portion and the horizontal portion.

The kit may further include a plurality of base connectors corresponding to the plurality of transition pieces, each of the plurality of base connectors may be configured to couple to the horizontal portion of a corresponding one of the plurality of transition pieces and may be configured to slide, with respect to the horizontal portion, toward and away from the vertical portion.

The kit may still further include a base configured to couple to the plurality of base connectors, a resilient dam configured to be releasably secured by each dam securing member of the plurality of transition pieces, and may also include a cover configured to couple to a third fastener on a top of each base connector of each of the plurality of transition pieces. In some aspects, the kit may further include an instruction manual providing directions on assembly and/or use of the sleep apnea device comprised of the bite block, the plurality of receivers, the plurality of transition pieces, the base, and the resilient dam. In a kit having the bite block and the plurality of receivers included as separate pieces, the kit may further include, for example, a bonding agent, an epoxy, a cement, or a glue to facilitate coupling of the plurality of receivers to a lingual surface of the bite block.

These and other aspects will become more fully understood upon a review of the detailed description, which follows. Other aspects, features, and implementations will become apparent to those of ordinary skill in the art, upon reviewing the following description of specific implementations in conjunction with the accompanying figures. While certain features may be discussed relative to certain implementations and figures below, all implementations can include one or more of the features discussed herein.

BRIEF DESCRIPTION OF THE DRAWINGS

Various features, nature, and advantages may become apparent from the detailed description set forth below when taken in conjunction with the drawings in which like reference characters identify correspondingly throughout. The drawings depict mechanical structures interacting with, adjacent to, and within each other. The mechanical structures are not drawn to scale. The illustrated spacing and size of the mechanical structures, the relative distances between the mechanical objects, and the relative sizes of the mechanical objects in comparison with one another are for illustrative purposes and are not limiting.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details.

Figure 1:
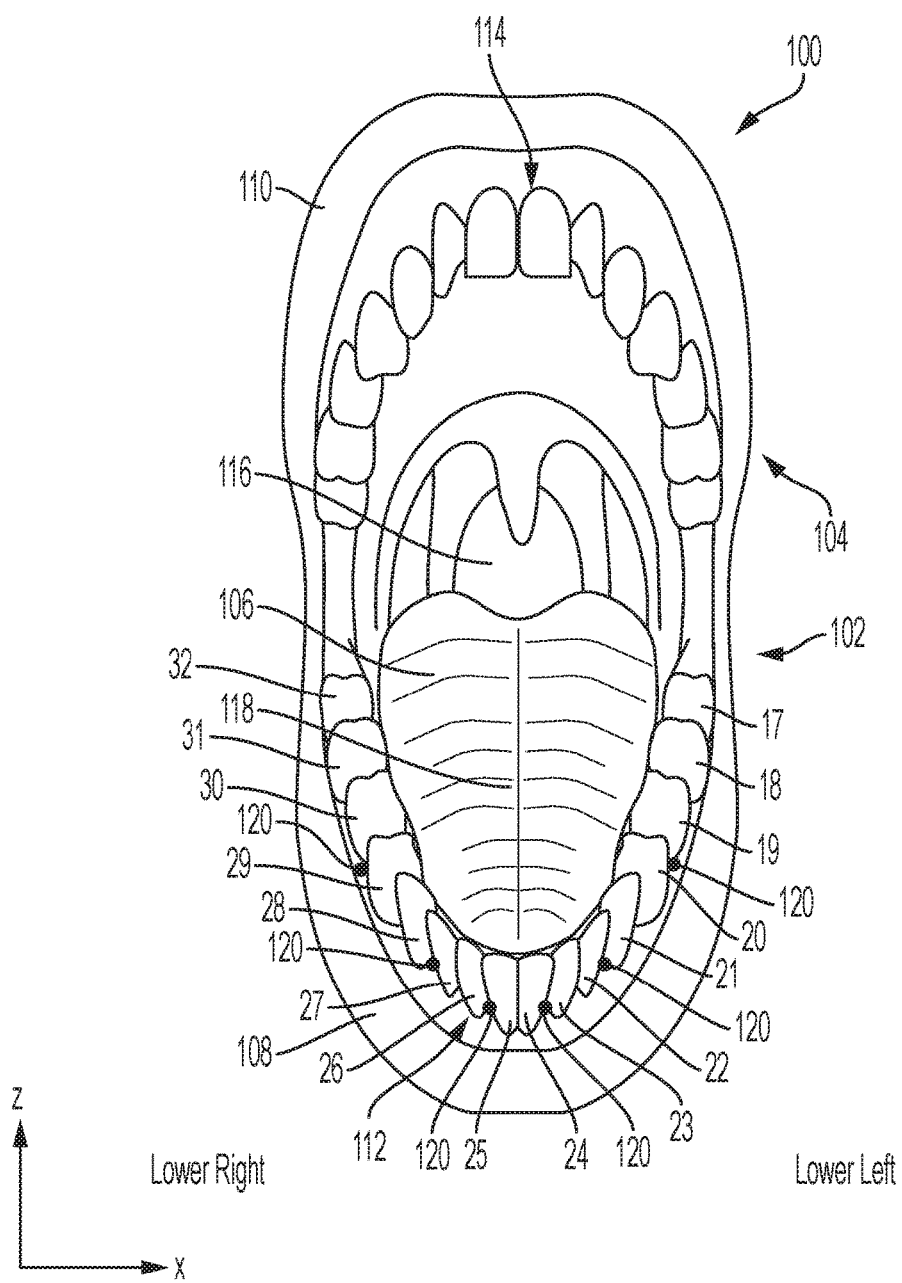
FIG. 1 is an illustration of an oral cavity and oropharynx of a human being.

FIG. 1 is an illustration of an oral cavity and oropharynx 100 of a human being (referred to as a patient). FIG. 1 depicts a lower jaw 102, an upper jaw 104, a tongue 106, the lower lip 108, upper lip 110, lower teeth 112 (mandibular), upper teeth 114 (maxillary), and an air passage (i.e., trachea), referred to herein as an airway 116. As used herein, a reference to the lower teeth 112 may mean one or more of the lower teeth 112 (e.g., one or at least two) or all the lower teeth 112 of the patient. As used herein, a reference to the upper teeth 114 may mean one or more of the upper teeth 114 (e.g., one or at least two) or all the upper teeth 114 of the patient. The upper surface of the tongue 106 may be referred to as the dorsum. The upper surface of the tongue 106 is divided by a groove into symmetrical halves by the median sulcus 118.

The teeth of the lower jaw are identified according to the American Dental Association tooth numbering system. The teeth of the lower left quadrant are: Wisdom Tooth (3rd Molar) 17, Molar (2nd Molar) 18, Molar (1st Molar) 19, Bicuspid (2nd) 20, Bicuspid (1st) 21, Canine (Eye tooth/Cuspid) 22, Incisor (Lateral) 23, and Incisor (Central) 24. The teeth of the lower right quadrant are: Wisdom Tooth (3rd Molar) 32, Molar (2nd Molar) 31, Molar (1st Molar) 30, Bicuspid (2nd) 29, Bicuspid (1st) 28, Canine (Eye tooth/Cuspid) 27, Incisor (Lateral) 26, and Incisor (Central) 25.

Figure 4:
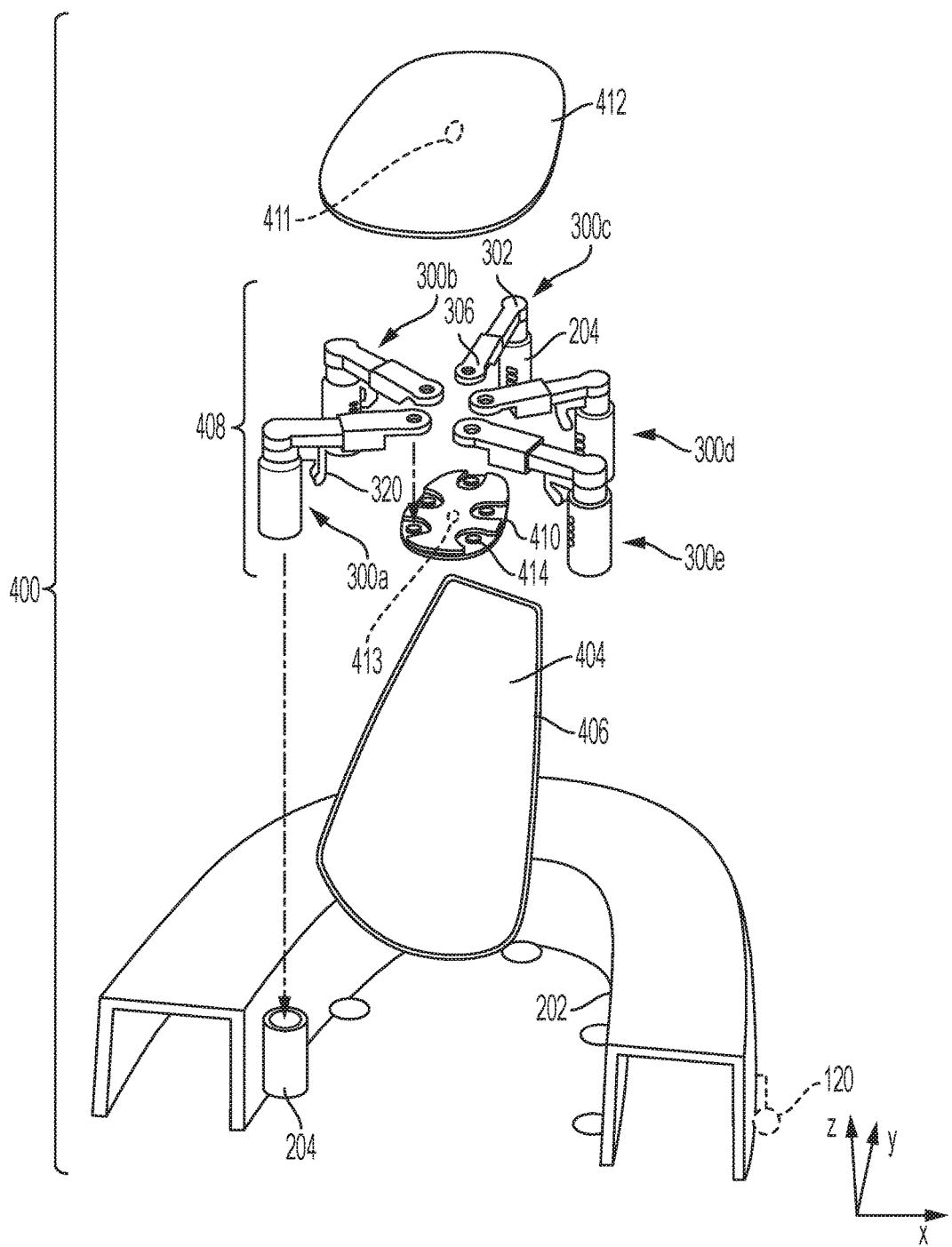
FIG. 4 is an exploded perspective view of one example of a sleep apnea device, according to aspects of the disclosure described herein.
Figure 13:
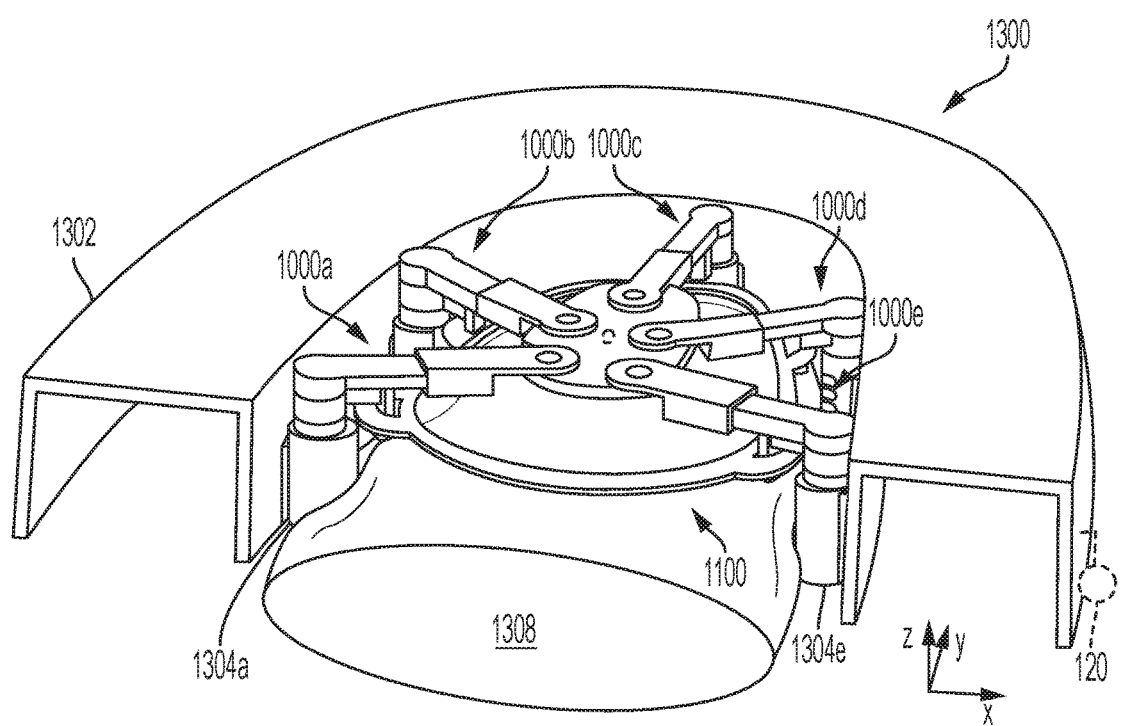
FIG. 13 is a perspective view of a sleep apnea device in an operative state where a portion of a tongue is illustrated to show the placement of the tongue relative to the bite block, the five frames, the resilient dam structure, and the base, according to aspects described herein.

FIG. 1 also depicts a plurality of clasps 120, which may be bonded, retained, or otherwise secured at a first end to the lower teeth 112 of the lower jaw 102 of a patient. Six clasps are depicted in FIG. 1; a fewer or greater number of clasps is within the scope of this disclosure. In FIG. 1, individual ones of the plurality of clasps 120 are located between the lower right Molar (1st Molar) 30 and Bicuspid (2nd) 29, between the lower right Bicuspid (1st) 28 and Canine (Eye tooth/Cuspid) 27, between the lower right Incisor (Lateral) 26 and Incisor (Central) 25, between the lower left Molar (1st Molar) 19 and Bicuspid (2nd) 20, between the lower left Bicuspid (1st) 21 and Canine (Eye tooth/Cuspid) 22, between the lower left Incisor (Lateral) 23 and Incisor (Central) 24. According to one example, a bite block (202, FIGS. 2 and 4) may be configured to be releasably secured to lower teeth 112 of a patient with a plurality of clasps 120, each of the plurality of clasps 120 having a first end configured to be secured (e.g., bonded to, retained by) to one or more of the lower teeth 112 of the patient and a second end, distal to the first end, configured to be releasably secured to the bite block 202. In some examples, the plurality of clasps 120 may be releasably secured to the bite block 202 by being configured to snap into or around receiving features (e.g., a depression, a raised rim or ridge) (not shown) of the bite block 202 or by being configured to grip (e.g., by friction or spring tension) the bite block 202. Other structures and methods of releasably securing the bite block 202 to the lower teeth of the patient, as known in the art, are within the scope of this disclosure. In some examples, the bite block 202 may alternatively be constructed to be releasably secured to the lower teeth 112 without use of the plurality of clasps 120. Exemplary and non-limiting illustrations of one clasp of the plurality of clasps 120 releasably secured to a bite block 202, 1302 are depicted in FIGS. 4 and 13, respectively. For exemplary and non-limiting purposes, the second end of the one clasp of the plurality of claps 120 is depicted as being a wire or spring. Other constructions and features of the second ends of the plurality of clasps are within the scope of this disclosure. Depictions of the plurality of clasps 120 are omitted from FIGS. 2, 6, and 7 to avoid cluttering the drawings.

Examples of sleep apnea devices (e.g., sleep apnea device 400 of FIG. 4 and sleep apnea device 1300 of FIG. 13) are presented. A sleep apnea device (400, 1300) may cover the tongue 106, without physically holding the tongue 106 captive (e.g., captivated by using a vacuum, or by a tongue tip holder device that holds the tip of the tongue which renders the tongue immobile). A resilient dam (e.g., resilient dam 404 of FIG. 4 and resilient dam 1104 of resilient dam structure 1100 of FIG. 11) of the sleep apnea device (400, 1300) may have a degree of resilience (e.g., an ability of a substance or object to spring back into shape; elasticity) that allows the tongue 106 to slidably move (e.g., move left, right, forward, backward, up, and down) against the resilient dam and prevents the tongue from sliding (or falling backward) into the airway 116 of the patient (e.g., sliding (or falling backward) into the airway 116 of the patient when the patient sleeps). The term resilient as used herein may mean a measure or ability of a substance to recoil or spring back into shape after bending, stretching, or being compressed. The slidable motion is free, or relatively free, and may depend, for example, on a degree of resilience of the resilient dam and the height of the resilient dam with respect to the bite block 202.

With use of the sleep apnea device (400, 1300) during sleep, the patient may swallow without the consequence of the tongue 106 of the patient falling into the airway 116 of the patient. When the sleep apnea device (400, 1300) as presented in the examples described herein is used, the patient will be able to rest and sleep without fear of sleep apnea.

Figure 2:
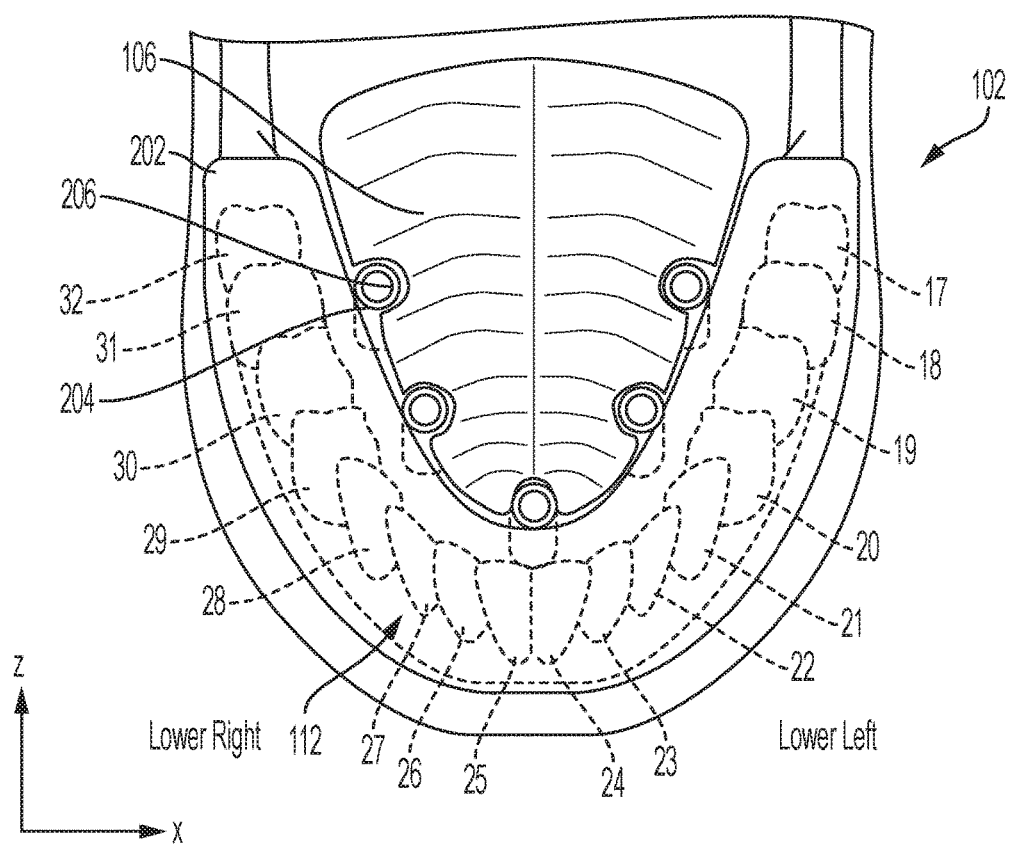
FIG. 2 illustrates a bite block having a plurality of receivers according to aspects of the disclosure described herein.

FIG. 2 illustrates a bite block 202 having a plurality of receivers 204 (e.g., five) according to aspects of the disclosure described herein. As used herein, individual ones of the plurality of receivers 204 may be singularly referred to as a receiver 204, while two or more may be collectively referred to as a plurality of receivers 204. Accordingly, the term "receiver" may refer to one receiver 204 and may alternatively refer to a collection of two or more, that is, a plurality of receivers 204. The meaning of the use of the term(s) receiver/plurality of receivers should be apparent from the context in which these terms are used.

The plurality of receivers 204 are shown as being cylindrical in shape for exemplary purposes only. The outer surfaces of each of the plurality of receivers 204 can be any shape known in the art, including but not limited to, cylindrical, square, elliptical, triangular, rectangular, or any other polygonal shape and/or curvilinear shape known in the art. Any one of the plurality of receivers 204 may be the same shape or a different shape as any other one of the plurality of receivers 204. In the exemplary illustration of FIG. 2, the plurality of receivers 204 are depicted as having an outer surface and a receiving portion 206 (e.g., an interior opening, an opening defined by an interior wall or walls of a receiver 204) that are both cylindrical. However, any receiver 204 may have an outer surface that is a different shape in comparison to the receiving portion 206. According to one aspect, the shape of the receiving portion 206 may correspond to the shape of the vertical portion 316 (FIG. 3A) of a transition piece (302, FIG. 3A) (or a portion thereof) to facilitate a coaxial slidable engagement of the vertical portion 316 (or portion thereof) within the receiving portion 206. According to one aspect, the shape of the receiving portion 206 and the shape of the vertical portion 316 (FIG. 3A) of a transition piece (302, FIG. 3A) (or a portion thereof) may both be cylindrical to facilitate both a coaxial slidable engagement of the vertical portion 316 (or portion thereof) within the receiving portion 206 and a rotatable engagement between the receiving portion 206 and the vertical portion 316 (or portion thereof).

In one example, the bite block 202 may be releasably secured to the lower teeth 112 and may articulate with respect to the upper teeth 114. Accordingly, in one example, the bite block 202 may be releasably secured to the lower teeth 112 and the sleep apnea device, such as sleep apnea device 400, FIG. 4 or sleep apnea device 1300, FIG. 13 may be configured to articulate with respect to the upper teeth 114. The lower teeth 112 are shown in phantom line through the bite block 202. The relative positions, both vertically and horizontally, of the plurality of receivers 204 with respect to the bite block 202 and tongue 106 are presented in FIG. 2 (and throughout the accompanying drawings) for illustrative purposes only.

In one example, an interior surface of the bite block 202 (i.e., a surface immediately adjacent to the lower teeth 112) may contact a top of (e.g., be positioned directly on top of) the lower teeth 112 and may articulate with respect to upper teeth 114. The bite block 202 may be constructed, for example, as a plastic tray, which fits over the lower teeth 112. In one example, the bite block 202 may be made from methyl-methacrylate, a hard plastic, which is used in denture fabrication. In one example, the biting surface of the bite block 202 may be made of a softer plastic, which occludes with the upper teeth 114. This softer plastic may be used to prevent bruxism, i.e., a clenching and grinding of the teeth during sleep, which can result in damage to the upper, opposing teeth.

The bite block 202 may be formed from transparent, semi-transparent, or opaque material and may be colored or tinted. The plurality of receivers 204 may be coupled to the bite block 202 (e.g., coupled to a lingual surface of the bite block 202) by being formed as one unit with the bite block 202, such that the bite block 202 and the plurality of receivers 204 are a unitary, or integral, structure. Conversely, the plurality of receivers 204 may be coupled to a lingual surface of the bite block 202 by use of a bonding agent, an epoxy, a cement, a glue, or the like as known to those in the art. As used herein, the word "lingual" means "on the side toward the tongue."

In the exemplary illustration of FIG. 2 the plurality of receivers 204 totals five. However, a fewer or greater number of the plurality of receivers 204 are within the scope of the disclosure. In the exemplary illustration of FIG. 2, the plurality of receivers 204 are approximately evenly spaced along the lingual surface of the bite block 202, but other spacing is within the scope of the disclosure.

Figure 3A:
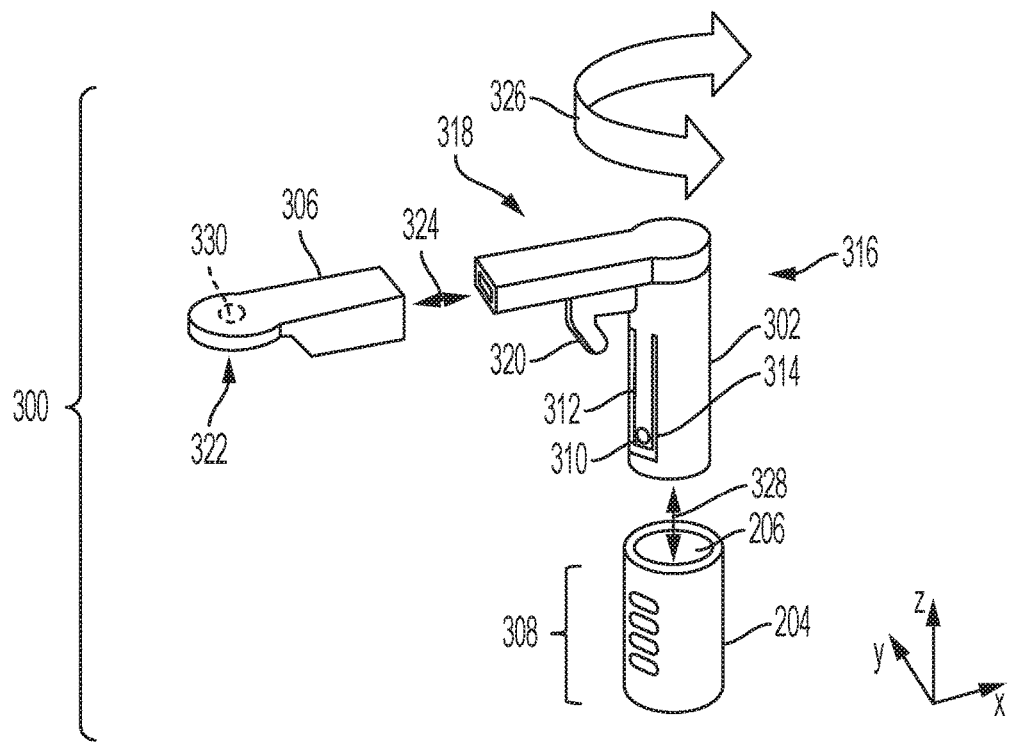
FIG. 3A is an exploded perspective view of one exemplary embodiment of a frame, including a transition piece, a receiver having a receiving portion, and a base connector, according to aspects of the disclosure described herein.

FIG. 3A is an exploded perspective view of one exemplary embodiment of a frame 300, including a transition piece 302, a receiver 204 having a receiving portion 206, and a base connector 306, according to aspects of the disclosure described herein. Although depicted as circular, a receiver 204 having any shape of outer surface and a receiving portion 206 having any shape inner surface into which a correspondingly shaped vertical portion 316 (or portion thereof) of a transition piece 302 may be received are within the scope of the disclosure. Components of the frame 300 may provide the ability to work equally for all sizes and shapes of jaws, long short, wide and narrow.

Figure 11:
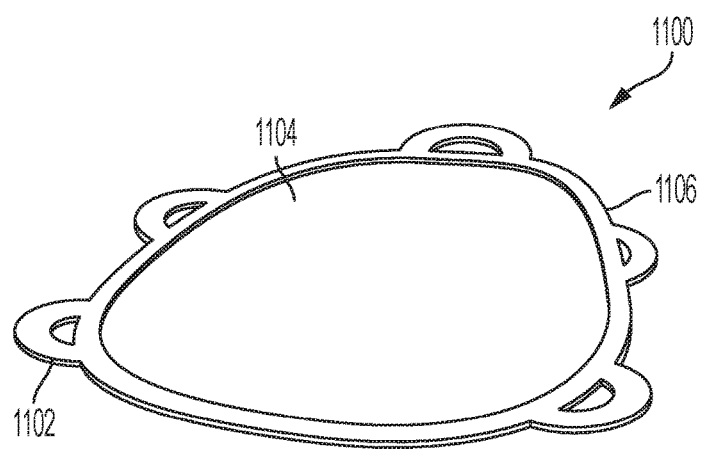
FIG. 11 depicts a resilient dam structure, according to aspects described herein.

The transition piece 302 may serve as a structural transition between vertical and horizontal planes. Accordingly, the transition piece 302 may include a vertical portion 316 and a horizontal portion 318. The terms vertical and horizontal are relative and not limiting. As used herein, references to vertical and horizontal directions or to vertical and horizontal planes are meant as references to two directions or planes that are substantially perpendicular to one another, regardless of their orientation with, for example, a horizon. The horizontal portion 318 may be configured to extend from the vertical portion 316 (e.g., form a substantially right angle relative to the vertical portion 316). According to some aspects, the horizontal portion 318 may extend from the vertical portion 316, and, using various exemplary descriptions, may extend from the vertical portion 316 toward an interior of an oral cavity of a patient, toward an interior of a mouth of a patient, toward a tongue of the patient. Each transition piece may also include a dam securing member 320. The dam securing member 320 may serve to releasably secure a peripheral member 406 (FIG. 4) of a resilient dam 404 (FIG. 4) and/or an attachment feature 1102 of a resilient dam structure 1100 (FIG. 11).

As depicted, the base connector 306 may have a hollow portion. The base connector 306 may receive a portion of the horizontal portion 318 of the transition piece 302 within the hollow portion of the base connector 306. The base connector may slidably engage with a portion of the horizontal portion 318. The base connector 306 may translate in the horizontal plane (e.g., move horizontally toward and/or away from the vertical portion 316) as shown by the first double headed arrows 324.

The base connector 306 may include a first fastener 322 (not visible) on a bottom of the base connector 306. The first fastener may be located toward an end of the base connector 306 that is distal to the vertical portion 316. As used herein a "fastener" and a "mating fastener" may be used herein to refer to individual parts of a pair of interlocking parts that may be used to releasably secure one member to another member and provide rotational movement between the one member and the other member (e.g., the member may rotate within the other member or vice versa). Examples of types of fasteners, or interlocking pairs of parts, may include a snap fastener, press stud, snap, popper, press buttons, and rivet. The preceding list is exemplary and non-limiting. To prevent repetitive explanation throughout the description, the terms fastener and mating fastener as used herein applies to the fasteners referred to herein as the first fastener 322, the second fastener 414, the third fastener 411, the fourth fastener 413, the plurality of fifth fasteners 330, the sixth fastener 1011, and the seventh fastener 1013. One respective pair of fastener and mating fastener may be the same or different from any other pair of fastener and mating fastener. It is noted that the rivet fastener passes through coaxial openings in at least a first member and a second member to secure the at least first member to the second member in a non-releasable yet rotationally possible manner. By way of example, turning to FIG. 3B, the first fastener 322 of a base connector 306 may couple to a second fastener 414 of a base 410. The base connector 306 and base 410 are releasably secured to one another via the use of the first fastener 322 and third fastener 411. The base connector 306 may rotate with respect to the base 410 because the first fastener 322 may rotate within the second fastener 414 (or vice versa), thus providing at least some rotational freedom between the base 410 and the base connector 306 coupled to the base 410.

Returning to FIG. 3A, the receiver 204 may have a receiving portion 206 defined by the interior sidewall(s) of the receiver 204 (e.g., a hollow interior). The receiver 204 may receive the vertical portion 316 (or a portion thereof) of the transition piece 302 within the receiving portion 206 of the receiver 204. According to one aspect, a vertical portion 316 of the transition piece 302 may couple to a corresponding receiver 204 by slidably and rotatably engaging with a receiving portion 206 of the corresponding receiver 204.

The receiver 204 may include a plurality of slots 308, which may be configured as a plurality of elongated horizontal rectangular openings (with rounded or square edges). Each of the plurality of slots 308 may be defined by sidewalls in a wall of the receiver 204. The plurality of slots 308 may be spaced apart from each other in the vertical plane, along a vertical length of the receiver 204. The plurality of slots 308 may be part of a detent mechanism 802 (FIG. 8) (e.g., a catch mechanism in a machine or structure that prevents motion until released). Each transition piece 302 may include a protuberance 310 (e.g., a thing that protrudes from something else) such as a button, a bulge, or a structure that will releasably fit into any of the plurality of slots 308 of the receiver 204 and that can allow the vertical portion 316 to rotatably transit, back and forth, across a predetermined angular distance. Once fit therein, the protuberance 310 may prevent vertical motion of the transition piece 302 with respect to the receiver 204. Accordingly, the transition piece 302 may provide stepped vertical translation (e.g., vertical movement or translation, up and down from, or in and out from) in the vertical plane with respect to the receiver 204 as shown by the third double headed arrows 328 and may provide limited rotational angular motion as shown by the double headed arrow 326.

Figure 3B:
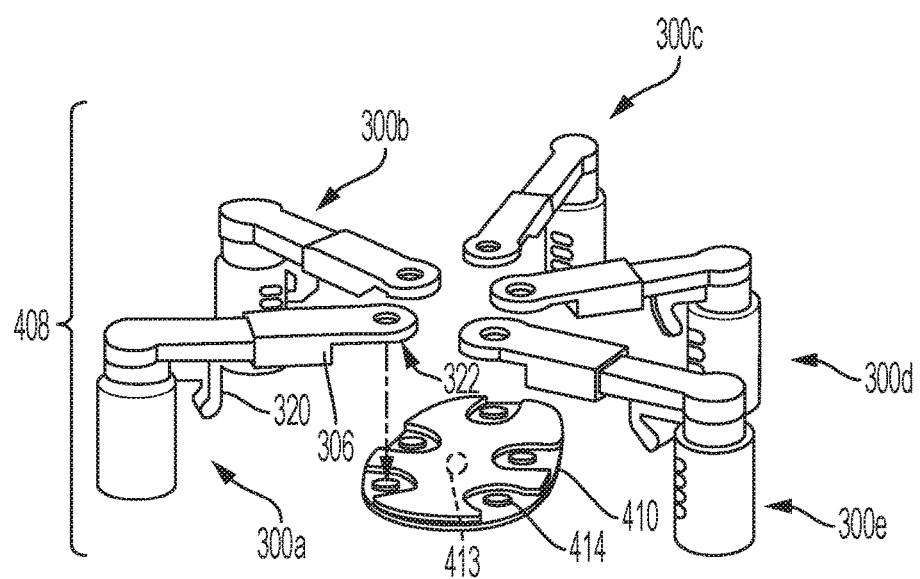
FIG. 3B is perspective view of one exemplary embodiment of a frame assembly, including five frames and a base, according to aspects of the disclosure described herein.

FIG. 3B is perspective view of one exemplary embodiment of a frame assembly 408, including five frames 300a, 300b, 300c, 300d, 300e and a base 410, according to aspects of the disclosure described herein. Frame assembly 408 is described in greater detail in connection with FIG. 4.

A First Description of a Sleep Apnea Device

FIG. 4 is an exploded perspective view of one example of a sleep apnea device 400, according to aspects of the disclosure described herein. According to one aspect, the sleep apnea device 400 may include a bite block 202 configured to be releasably secured to lower teeth of a lower jaw of a patient. By way of example, one clasp of a plurality of clasps 120 is illustrated in an operational configuration, where it is releasably secured to at least one of the lower teeth (e.g., 112, FIG. 1) (not shown) of a patient. The plurality of claps 120 may be releasably secured to the bite block 202 by being configured to snap into or around receiving features (e.g., a depression, a raised rim or ridge) (not shown) of the bite block 202 or by being configured to grip (e.g., by friction or spring tension) the bite block 202.

The sleep apnea device 400 may also include a plurality of receivers 204 coupled to a lingual surface of the bite block 202 (i.e., on a side of the bite block 202 that is adjacent to the tongue of a patient). The bite block 202 is illustrated with only one of the plurality of receivers 204 (where the plurality in this example refers to five) to reduce clutter. Positions of the remaining ones of the plurality of receivers 204 are identified with circles along the bottom inner perimeter of the bite block 202.

The sleep apnea device 400 may further include a plurality of transition pieces 302 received at one end by corresponding ones of the plurality of receivers 204. The sleep apnea device 400 may further include a plurality of base connectors 306 received at the other end by the corresponding ones of the plurality of transition pieces 302.

The sleep apnea device 400 may further include a base 410 having a top side and a bottom side, coupled to ends of the plurality of base connectors 306. According to some aspects, the base 410 may include a plurality of second fasteners 414, fixed to or integral with the top side of the base 410, each of the plurality of second fasteners 414 configured to releasably and rotatably couple to a corresponding first fastener 322, fixed to or integral with a bottom side of a corresponding one of the plurality of base connectors 306.

The sleep apnea device 400 may further include a resilient dam 404 configured to be releasably secured by the dam securing members 320 of each of the plurality of transition pieces 302. In greater detail, the resilient dam 404 may include a peripheral member 406 on a circumference of the resilient dam 404 and the peripheral member 406 may be configured to be releasably secured by each dam securing member of the plurality of transition pieces. According to some aspects, the peripheral member 406 may be configured to be releasably secured by and/or to each dam securing member of the plurality of transition pieces. As used herein, the word "circumference" may refer to "the enclosing boundary of a curved geometric figure, for example an ellipse or a circle." According to some aspects, each transition piece 302 of the plurality of transition pieces 302, which is coupled to the peripheral member 406 via the dam securing member 320, positions the resilient dam 404 between the base 410 and the tongue (106, FIG. 7). In an operational configuration, the resilient dam 404 may be adjacent to and/or touching the tongue. The plurality of transition pieces 302 may be raised or lowered, is a stepwise manner (by application of the detent mechanism 802 discussed in connection with FIG. 8), to accommodate different thicknesses of tongues.

The sleep apnea device 400 may further include a cover 412 having a top side and a bottom side. The cover 412 may be configured to couple to the base 410. The cover 412 may be provided to shield the roof of the patient's mouth from contact with the plurality of frames 300a-300e. The cover 412 resides above or over the frame assembly 408. According to a first option, the cover 412 may be configured to couple to the base 410 using a third fastener 411, fixed to or integral with the bottom side of the cover 412, that couples to a fourth fastener 413, fixed to or integral with a top side of the base 410. According to a second option, the cover 412 may be configured to couple to the base 410 using a plurality of fasteners (not shown), fixed to or integral with the bottom side of the cover 412, that couple to a corresponding plurality of fifth fasteners 330, each of the plurality of fifth fasteners 330 fixed to or integral with a top side of a corresponding base connector 306. In the second option, the cover 412 couples to the base 410 via the plurality of base connectors 306. In accordance with the first option, the fasteners may be a rivet that passes through coaxial holes in the cover 412 and base 410. In accordance with the second option, the fasteners may be a plurality of rivets that pass through a plurality of coaxial holes in the cover 412, the plurality of base connectors 306, and the base 410. In some examples, one or more of the rivets may be replaced by columns or dowels that are fixed, at opposing ends, to the cover 412 and the base 410. For any rivet, column, or dowel passing through a base connector 306, the hole in the base connector 306 (through which the rivet, column, or dowel passes) may provide clearance to allow the base connector 306 to rotate freely with respect to the rivet, column, or dowel.

An Alternative Second Description of a Sleep Apnea Device

By way of an alternative description and according to another aspect, the sleep apnea device 400 may include a bite block 202. The bite block 202 is illustrated with only one of the plurality of receivers 204 (where the plurality in this example refers to five) to reduce clutter. Positions of the remaining ones of the plurality of receivers 204 are identified with circles along the bottom inner perimeter of the bite block 202.

The sleep apnea device 400 may also include a frame assembly 408 including a plurality of frames 300*a*, 300*b*, 300*c*, 300*d*, 300*e* and base 410. Each of the plurality of frames 300*a*-300*e* is similar to the frame 300 of FIG. 3A. It is noted that although the receiver 204 is coupled to the bite block 202, the receiver 204 is referred to, and described herein, as being a part of the frame 300 of FIG. 3A; accordingly each of the plurality of frames 300*a*-300*e* may include a respective receiver 204, even though that receiver 204 may be coupled to, or formed integral with, the bite block 202.

According to some aspects the frame assembly 408 may include a base 410. The base 410 may include a plurality of second fasteners 414 (e.g., a snap ring or a clip) that releasably and rotatably couples the base 410 to each of a plurality of base connectors 306. The second fastener 414 may be formed with or coupled to a base 410. The first fastener 322 of the base connector 306 of each of the plurality of frames 300*a*-300*e* may couple to and may rotate, one within the other, with respective ones of the second fasteners 414 of the base 410, thus providing at least some rotational freedom between the base 410 and each base connector 306 coupled to the base 410.

The sleep apnea device 400 may also include a resilient dam 404 having a peripheral member 406. The peripheral member 406 may be configured to be releasably secured by each of the dam securing members 320 of each of the plurality of frames 300*a*-300*e*. As used herein, a first feature releasably secured by a second feature encompasses the first feature being releasably secured to the second feature. According to some examples, the peripheral member 406 of the resilient dam 404 may have a circular cross section. Other cross-sections (e.g., star, pentagonal, hexagonal, square, rectangular) that are configured to be releasably secured by a dam securing member 320 of each of the plurality of frames 300*a*-300*e* of the frame assembly 408 are within the scope of the disclosure. The shape of the dam securing member 320 as illustrated in FIG. 3A, FIG. 3B, and/or FIG. 4 is illustrative and non-limiting.

The sleep apnea device 400 may further include a cover 412 having a top side and a bottom side. The cover 412 may be configured to couple to the base 410. The cover 412 may be provided to shield the roof of the patient's mouth from contact with the plurality of frames 300*a*-300*e*. The cover 412 resides above or over the frame assembly 408. According to a first option, the cover 412 may be configured to couple to the base 410 using a third fastener 411, fixed to or integral with the bottom side of the cover 412, that couples to a fourth fastener 413, fixed to or integral with a top side of the base 410. According to a second option, the cover 412 may be configured to couple to the base 410 using a plurality of fasteners (not shown), fixed to or integral with the bottom side of the cover 412, that couple to a corresponding plurality of fifth fasteners 330, each of the plurality of fifth fasteners 330 fixed to or integral with a top side of a corresponding base connector 306. In the second option, the cover 412 couples to the base 410 via the plurality of base connectors 306. In accordance with the first option, the fasteners may be a rivet that passes through coaxial holes in the cover 412 and base 410. In accordance with the second option, the fasteners may be a plurality of rivets that pass through a plurality of coaxial holes in the cover 412, the plurality of base connectors 306, and the base 410. In some examples, one or more of the rivets may be replaced by columns or dowels that are fixed, at opposing ends, to the cover 412 and the base 410. For any rivet, column, or dowel passing through a base connector 306, the hole in the base connector 306 (through which the rivet, column, or dowel passes) may provide clearance to allow the base connector 306 to rotate freely with respect to the rivet, column, or dowel.

According to some aspects, each transition piece 302, which is coupled to the peripheral member 406 via the dam securing member 320, positions the resilient dam 404 between the base 410 and the tongue (106, FIG. 7). the plurality of transition pieces 302 may be raised or lowered, is a stepwise manner (by application of the detent mechanism 802 discussed in connection with FIG. 8), to accommodate different thicknesses of tongues.

An Alternative Third Description of a Sleep Apnea Device

According to still another aspect, one way to explain an example of a sleep apnea device 400 according to the disclosure may be to first note that the sleep apnea device 400 may give the user a superior professional approach to prevent sleep apnea. The mouth guard (e.g., bite block 202) may be fabricated for each user with different sized and shaped mandibles for custom fit. Still, the sleep apnea device 400 allows for use of a standardized device (e.g., frame assembly 408 or frame assembly 408 plus resilient dam 404 or frame assembly 408 plus resilient dam 404 plus cover 412) that works for all individuals because the majority of the standardized device is added to the individual's mouth guard (e.g., bite block 202).

As illustrated in FIG. 4, according to one aspect, the sleep apnea device 400 may include five individual frames (e.g., 300*a*, 300*b*, 300*c*, 300*d*, 300*e*), although a smaller or larger number of frames are within the scope of the disclosure. Each frame (e.g., frame 300) may include at least two parts. A first part may be a horizontal component (e.g., base connector 306) with, for example, an opening at the end, to attach with a rivet, screw, bolt, snap ring, clip, or anything to a holder of parts (e.g., base 410). According to some aspects, the horizontal part may also couple to a protective cover (e.g., cover 412). A second part (e.g., transition piece 302) may include two parts: the first part (of the second part) is a horizontal part (e.g., horizontal portion 318), which slides in and out of the horizontal component (e.g., base connector 306) and the second part (of the second part) is a vertical part (e.g., vertical portion 316) which terminates in a receiver 204 and thereby couples the device (e.g., remaining parts of the sleep apnea device 400) to the mouth guard (e.g., bite block 202). The second part (e.g., transition piece 302) also has a dam securing member 320.

The five frames (e.g., 300*a*-300*e*) enable the device (e.g., sleep apnea device 400) to lengthen and/or shorten so that the five frames can be used for the appropriate jaw sizes. The five frames change in length and angle automatically, by the moving in and out of the horizontal component (e.g., base connector 306 relative to horizontal portion 318) and by rotating forwards and backwards (e.g., clockwise and counter clockwise) in the receiver 204 and therefore provide for width adjustments to suit all patients.

Figure 5:
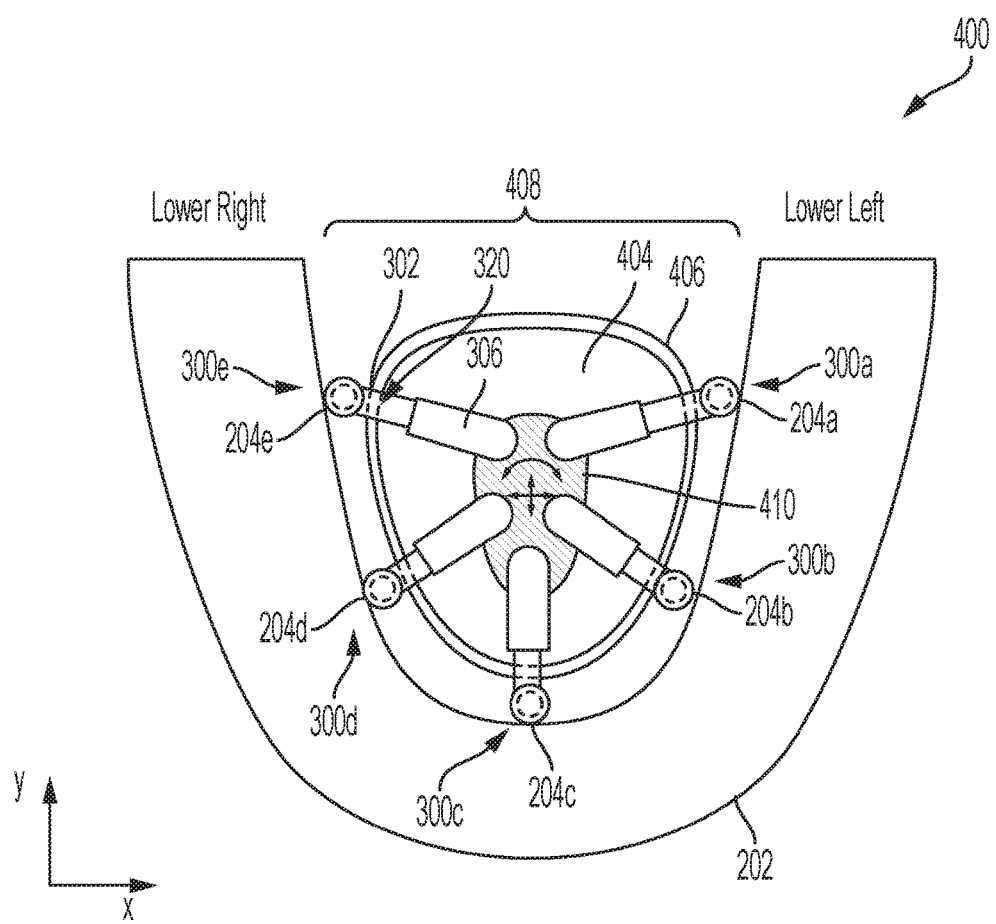
FIG. 5 is a top view of a sleep apnea device in an operational configuration, according to aspects of the disclosure described herein.

FIG. 5 is a top view of a sleep apnea device 400 in an operational configuration, according to aspects of the disclosure described herein. The x-axis and y-axis coordinate system is shown on the drawing. The z-axis extends out of the page. Each axis is perpendicular to the other axes. The sleep apnea device 400 may include a bite block 202. The bite block 202 is illustrated with five frames 300a-300e, each frame including a receiver 204 coupled to (or integral with) the bite block 202, a transition piece 302 (see FIG. 3A), a base connector 306 (see FIG. 3A), and a dam securing members 320, on an underside of the transition piece 302 (shown in phantom line).

In the embodiment of FIG. 5, receiver 204a and receiver 204e are placed on the right and left inner (lingual) side of the bite block 202 between the first and second lower (mandibular) molars, receiver 204b and receiver 204d are placed on the right and left inner (lingual) side of the bite block 202 between the first and second lower (mandibular) bicuspids, and receiver 204c is placed on the inner (lingual) side of the bite block 202 between the third and fourth lower (mandibular) incisors. Other positioning is within the scope of the disclosure.

Several advantages may be derived from this arrangement. The sleep apnea device 400 may accommodate differently sized tongues as the bite block 202 can be shaped (e.g., molded, configured) to fit each given patient. The frame assembly 408 may have a configuration which is universal and standardized and may therefore be adaptable to a bite block 202 of any shape. The sleep apnea device 400 may allow for simple adjustments of the frame assembly 408 (by, for example, height adjustment of the resilient dam 404, by height adjustment of the transition pieces 302 with respect to the plurality of receivers 204). The sleep apnea device 400 may allow for a visual check by a dentist to ascertain the most comfortable position of the resilient dam 404. In one example, a visual check may be enabled by use of a clear, or semi-transparent, resilient dam 404, so that a dentist can visually ascertain the most comfortable position for the resilient dam 404. Additionally, with use of the sleep apnea device 400, the tongue 106 is not held hostage (in contrast to devices that hold the tongue 106 physically by use of suction or clips), which allows the patient to sleep comfortably and without being disturbed. The sleep apnea device 400 may permit the tongue 106 to move as freely as normally possible, apart from the tongue's 106 falling backwards into the airway 116 of the patient during sleep, which otherwise would result in sleep apnea and interfere with the patient's sleep. With use of the sleep apnea device 400 as exemplified herein, the tongue 106 may be comfortably restrained (e.g., by the pressure of the resilient dam 404 on the surface of the tongue 106) and thereby may not cause a disruption in sleep. In summary, the resilient dam 404 of the sleep apnea device 400 may apply pressure over a broad surface of the tongue 106 to prevent the tongue 106, during sleep, from falling back and occluding the airway 116, which would cause sleep apnea.

As illustrated in FIG. 5, the base 410 of the sleep apnea device 400 may have limited translational movement and limited rotational movement in an operational state. The plurality of frames 300a-300e are rotatably (to a limited extent) engaged with the corresponding plurality of receivers 204a-204e (e.g., each of the plurality of transition pieces 302 has a predetermined degree of rotation allowed about the z-axis (e.g., yaw)). A stepped translation of the transition piece 302 relative to the receiver 204, in the z-axis (e.g., up and down), may be selectively set (e.g., a dentist may change the height of the resilient dam 404 with respect to, for example, the bite block 202 in stepped increments, but a patient would generally not change the height). In other words, translation of each of the plurality of transition pieces 302 along the z-axis may be selectively fixed in predetermined stepped increments (corresponding to the distances between each pair of slots in the plurality of slots 308). A lengthwise (longitudinal) translation is provided by each base connector 306 slidably coupled to its respective transition piece 302. The lengthwise translation of the base connectors 306 and limited rotational freedom of the transition pieces 302 seated in the plurality of receivers 204, and the rotational freedom of the first fasteners 322, on an underside of the base connectors 306, relative to the second fasteners 414 on a top of the base 410, permits, and/or provides for, the base 410 to have left-right translation in the x-axis, forward-backward translation in the y-axis, and rotation about the z-axis as shown by the arrows projected onto the base 410. In other words, the base 410 may be configured to have left-right translation in the x-axis, forward-backward translation in the y-axis, and rotation about the z-axis (where the z-axis may move relative to, or with, a rotational center-point of the base 410) in response to movements of the tongue 106 influencing a position of the base 410 (via the tongue's influence on the resilient dam 404). In still other words, the base 410 may be configured to translate along the x-axis, translate along the y-axis, and rotate about the z-axis in response to movements of the tongue 106 influencing a position of the base 410 (via the tongue's influence on the resilient dam 404).

Figure 6:
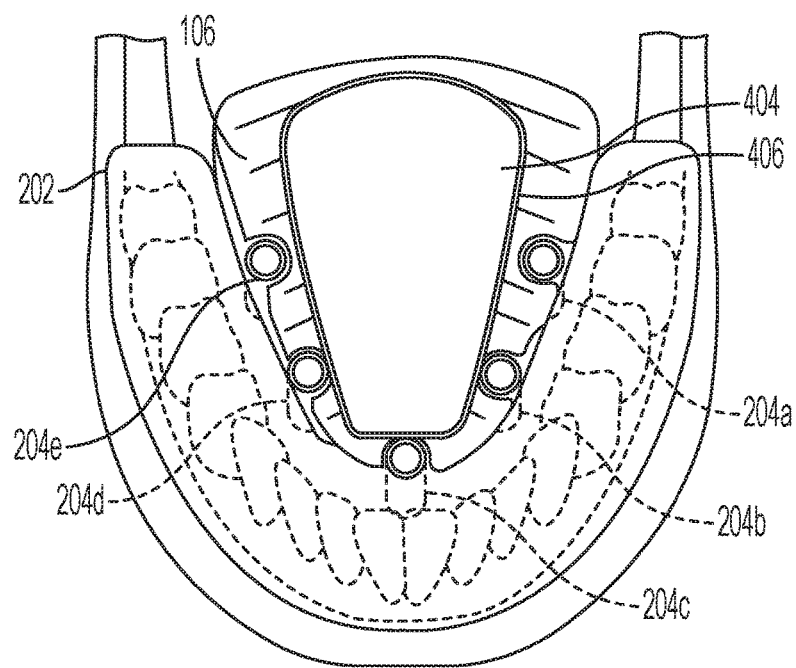
FIG. 6 is a front perspective view of a resilient dam in place on a surface of the tongue of FIG. 2, all in accordance with aspects of the disclosure described herein.

FIG. 6 is a front perspective view of a resilient dam 404 in place on a surface of the tongue 106 of FIG. 2, all in accordance with aspects of the disclosure described herein. It is noted that in operation, when the tongue 106 is at rest and the patient is not swallowing, at least a part (e.g., typically a rearward part) of the resilient dam 404 may be spaced apart from the surface of the tongue 106 and does not touch the tongue 106. Also, in operation, when the patient is swallowing, the full surface of the resilient dam 404 may touch the top surface of the tongue 106, applying pressure over a broad surface of the tongue 106, and prevent the tongue 106 from sliding (or falling backward) into the airway 116 of the patient (e.g., sliding (or falling backward) into the airway 116 of the patient when the patient sleeps). FIG. 6 is not meant to imply that the resilient dam 404 always rests entirely on the tongue 106. FIG. 6 is provided to show one example of the resilient dam 404 in relation to the tongue 106 as it would be if held by the frame assembly 408 (e.g., FIG. 3B) when the frame assembly 408 is seated in the plurality of receivers 204 coupled to the bite block 202.

Figure 7:
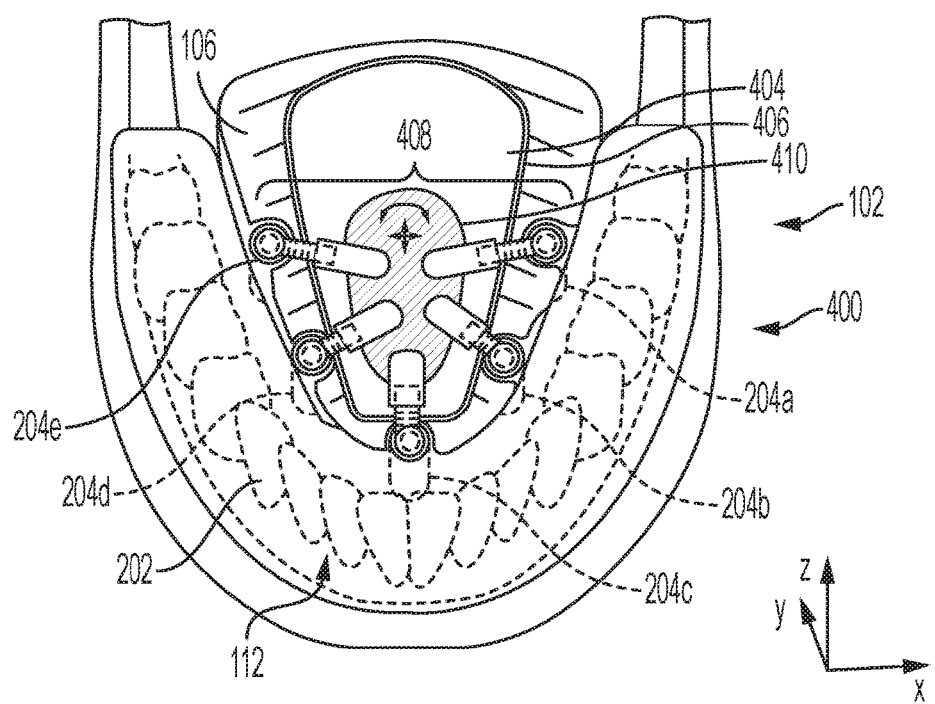
FIG. 7 is a front perspective view of a sleep apnea device, in place in a patient's mouth, all in accordance with aspects of the disclosure described herein.

FIG. 7 is a front perspective view of a sleep apnea device 400, in place in a patient's mouth, all in accordance with aspects of the disclosure described herein. The sleep apnea device 400 may include a bite block 202 coupled to or integrated as a unit with a plurality of receivers 204a-204e. The sleep apnea device 400 may also include a frame assembly 408, which includes a resilient dam 404 coupled to a base 410 (via the transition pieces and base connectors). As described in connection with FIG. 5, the base 410 may be configured to have left-right translation in the x-axis, forward-backward translation in the y-axis, and rotation about the z-axis (where the z-axis may move relative to, or with, a rotational center-point of the base 410) in response to movements of the tongue 106 influencing a position of the base 410 (via the tongue's influence on the resilient dam 404). In still other words, the base 410 may be configured to translate along the x-axis, translate along the y-axis, and rotate about the z-axis in response to movements of the tongue 106 influencing a position of the base 410 (via the tongue's influence on the resilient dam 404).

Figure 8:
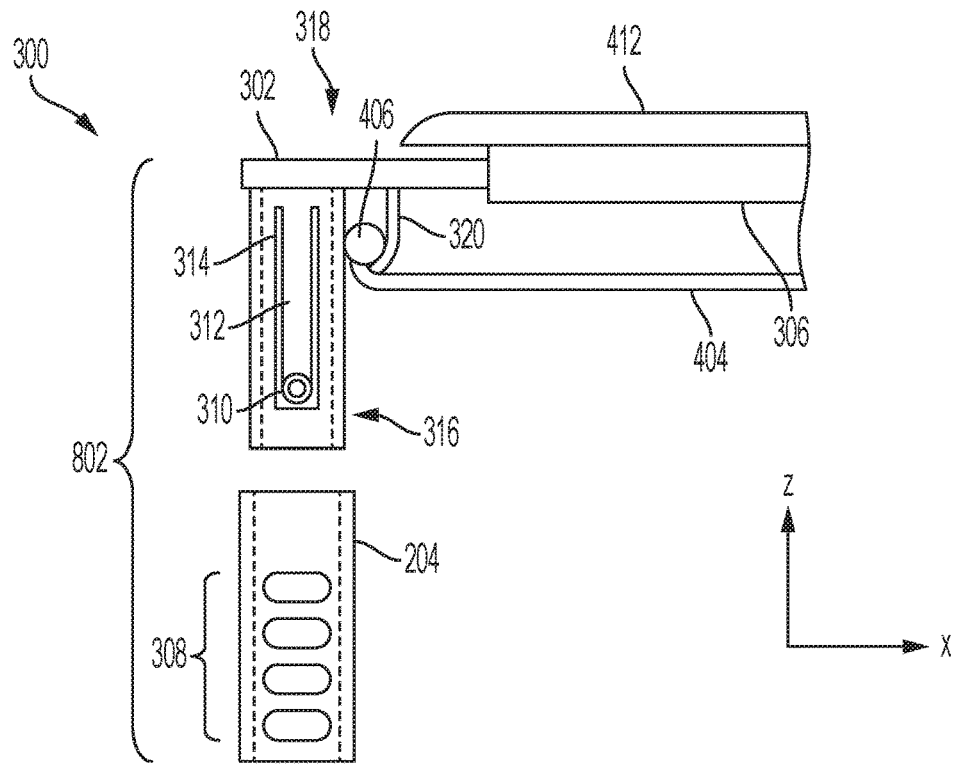
FIG. 8 is a side (elevation) view of a frame, including a receiver, according to aspects of the disclosure described herein.

FIG. 8 is a side (elevation) view of a frame 300, including a receiver 204, according to aspects of the disclosure described herein. An x-y-z coordinate system is indicated, where the z-axis represents up and down, the x-axis represents left and right, and the y-axis is pointed into the sheet of the drawing and represents in and out. Each axis is perpendicular to the other axes. The sheet of the drawing is parallel to the x-z plane, while the x-y plane is perpendicular to the sheet of the drawing. The receiver 204 (e.g., one receiver 204 of a plurality of receivers (not shown)) is shown in a spaced apart relationship with the frame 300. A portion of a base connector 306 is slidably engaged with the horizontal portion 318 of the transition piece 302 of the frame 300. A portion of a cover 412 and a portion of the resilient dam 404 are depicted. The dam securing member 320 is illustrated as being in a releasably secured relationship with a peripheral member 406 of the resilient dam 404. A vertical portion 316 of the transition piece 302 is shown just prior to being inserted into, or just after being withdrawn from, the receiver 204.

A detent mechanism 802 may be formed by a first feature of the vertical portion 316 of the transition pieces 302 engaged with a second feature of a corresponding receiver 204. For example, the first feature of the vertical portion 316 may include a biasing element 312 (e.g., a resilient and/or spring-like lever), a protuberance 310 at a movable (e.g., depressible) end of the biasing element 312, and a receiving portion 314 defined by interior sidewalls of the vertical portion 316 of the transition piece 302, where the biasing element 312 is fixed to and/or integral with the vertical portion 316 of the transition piece 302 at a first end of the receiving portion 314 and has the protuberance 310 fixed to and/or integral with a second end of the biasing element 312 (the second end being distal to the first end). The biasing element 312 and protuberance 310 are configured such that when a force is exerted on the protuberance 310 the biasing element 312 bends, from a neutral position, into the receiving portion 314, and when the force is removed from the protuberance 310 the biasing element 312 resiliently springs back to the neutral position. The second feature of receiver 204 may include the plurality of slots 308 of the receiver 204. The protuberance 310 may be received in any of the plurality of slots 308 and may travel within the slot (from end to end) in a horizontal x-y plane.

Figure 9:
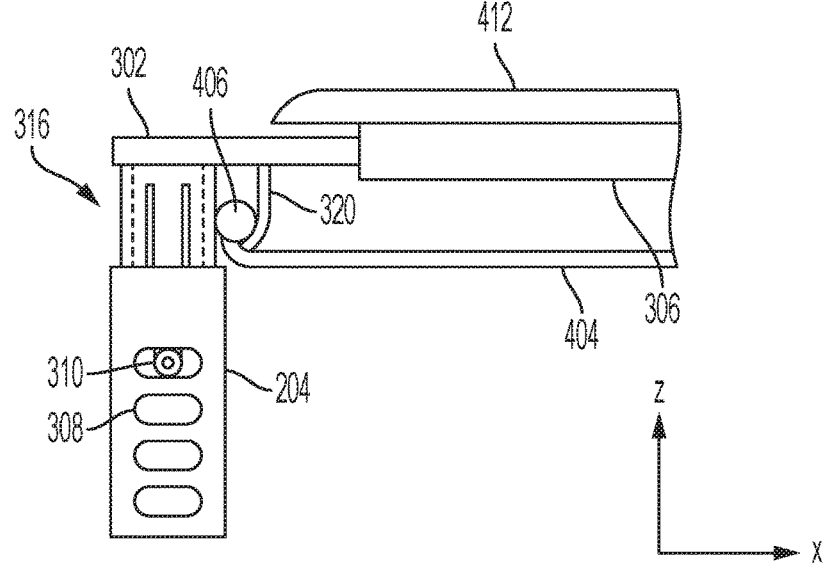
FIG. 9 is a magnified side (elevation) view of the frame of FIG. 8, where the vertical portion of the transition piece is slidably engaged with the receiver, according to aspects of the disclosure described herein.

FIG. 9 is a magnified side (elevation) view of the frame 300 of FIG. 8, where the vertical portion 316 of the transition piece 302 is slidably engaged with the receiver 204, according to aspects of the disclosure described herein. An x-y-z coordinate system is indicated, where the z-axis represents up and down, the x-axis represents left and right, and the y-axis is pointed into the sheet of the drawing and represents in and out. Each axis is perpendicular to the other axes. The sheet of the drawing is parallel to the x-z plane, while the x-y plane is perpendicular to the sheet of the drawing. FIG. 9 may demonstrate that each vertical portion 316 (of a plurality of transition pieces 302) may be coupled to a corresponding receiver 204 by slidably engaging with a receiving portion 206 of the corresponding receiver 204. The protuberance 310 is depicted as being received within the uppermost slot of the plurality of slots 308. It will be understood that the protuberance 310 may be received in any of the plurality of slots 308. The transition piece 302 may obtain stepped vertical translation (e.g., translation along the z-axis) by depressing the protuberance 310 such that the protuberance 310 (and the transition piece to which it is coupled) can be moved upward or downward (e.g., translated along the z-axis) to be received by another one of the plurality of slots 308. Accordingly, the detent mechanism 802, formed by the first feature of the vertical portion 316 of the transition pieces 302 engaged with the second feature of the receiver 204, may be configured to provide a stepped vertical translation (translation along the z-axis) of the transition piece 302 with respect to the receiver 204.

When a vertical height of the protuberance is less than a height of a respective one of the plurality of slots 308, and a horizontal width of the protuberance 310 is less than a horizontal length of the respective one of the plurality of slots 308 (as depicted in FIGS. 8 and 9), the protuberance 310 may be received in the respective one of the plurality of slots 308 and may travel horizontally within the respective one of the plurality of slots 308. When the protuberance 310 is cylindrical and the diameter of the protuberance 310 is less than the height of the respective one of the plurality of slots 308 (as depicted in the exemplary illustrations of FIGS. 8 and 9), the protuberance 310 may travel horizontally within the respective one of the plurality of slots 308. Because the protuberance 310 is coupled to the vertical portion 316 of the transition piece 302, the protuberance 310 may allow a predefined angular rotation (e.g., a limited rotational movement) of the transition piece 302 (around the z-axis) with respect to the receiver 204.

Accordingly, a detent mechanism 802, which may be formed by a first feature of the vertical portion 316 of each transition piece 302 engaged with a second feature of a corresponding receiver 204, may be configured to provide a stepped vertical translation (translation along the z-axis) of the transition piece 302 with respect to the corresponding receiver 204 and provide a predefined angular rotation (around the z-axis) of the transition piece 302 with respect to the corresponding receiver 204. According to one example, the width of the protuberance 310 and the length of the plurality of slots 308 may be configured to provide a predefined angular rotation of about ±5, ±10, ±20, or ±45 degrees of rotational freedom. According to another example, the width of the protuberance 310 and the length of the plurality of slots 308 may be configured to provide a predefined angular rotation that may be greater than or equal to about ±10 degrees and less than or equal to about ±45 degrees with respect to a central vertical axis of the receiver 204. According to still another example, the width of the protuberance 310 and the length of the plurality of slots 308 may be configured to provide a predefined angular rotation that may be greater than or equal to about ±10 degrees and less than or equal to about ±35 degrees with respect to a central vertical axis of the receiver 204. When the base 410 is configured to rotate with respect to each of the plurality of base connectors 306 via a rotation of each first fastener 322 within or around each respective (mated) second fastener 414, and each of the plurality of base connectors 306 are coupled to and configured slide laterally along a lateral (e.g., lengthwise) axis of each respective horizontal portion 318 of a plurality of transition pieces 302, and each vertical portions 316 of the plurality of transition pieces 302 is configured to rotate by a predefined angular rotation (e.g., a limited rotational movement) of the transition piece 302 (around the z-axis) with respect to each of a corresponding plurality the receivers 204, then the base 410 may translate along the x-axis, translate along the y-axis, and rotate about the z-axis in response to movements of the tongue influencing a position of the base 410 via the influence of the tongue (e.g., a broad surface area of the tongue) on the resilient dam 404.

The biasing element 312 and protuberance 310 may be substituted with, for example, a button or ball backed up by a spring or other resilient device/structure, so long as the button or ball fits within the slots of the plurality of slots 308 and is configured to travel horizontally within the horizontal length of the one of the plurality of slots 308 in the same or similar way and to the same degree as the protuberance 310.

With respect to the resilient dam 404 and the peripheral member 406 of the resilient dam 404, FIGS. 8 and 9 depict, for exemplary and non-limiting purposes, the peripheral member 406 of the resilient dam 404 in a state where it is releasably secured between an outer wall of the vertical portion 316 of the transition piece 302 and inner (facing) surfaces of the dam securing member 320. In a first example, the outer wall of the vertical portion 316 of the transition piece 302 and inner (facing) surfaces of the dam securing member 320 are both substantially rigid and the peripheral member 406 may be configured to elastically deform and squeeze into the open space between the outer wall of the vertical portion 316 of the transition piece 302 and inner (facing) surfaces of the dam securing member 320. Deformation may be achieved, for example, by stretching the portion of the peripheral member 406 along its central axis to reduce the diameter of that portion of the peripheral member 406. In a second example, the outer wall of the vertical portion 316 of the transition piece may be substantially rigid while the dam securing member 320, or a portion of the dam securing member 320 may be configured to be flexible. In this second example, the dam securing member 320 or a portion of the dam securing member 320 may be configured to resiliently deform, or flex out of shape, thus permitting, and/or providing for, a portion of the peripheral member 406 of the resilient dam 404 to be inserted and releasably secured within the open space defined between the outer wall of the vertical portion 316 of the transition piece 302 and inner (facing) surfaces of the dam securing member 320. In a third example, each of a portion of the peripheral member 406 of the resilient dam 404 and the dam securing member 320 or a portion of the dam securing member 320 may resiliently deform to permit, and/or provide for, insertion of the portion of the peripheral member 406 of the resilient dam 404 to be inserted and releasably secured within the open space defined between the outer wall of the vertical portion 316 of the transition piece 302 and inner (facing) surfaces of the dam securing member 320.

Figure 10:
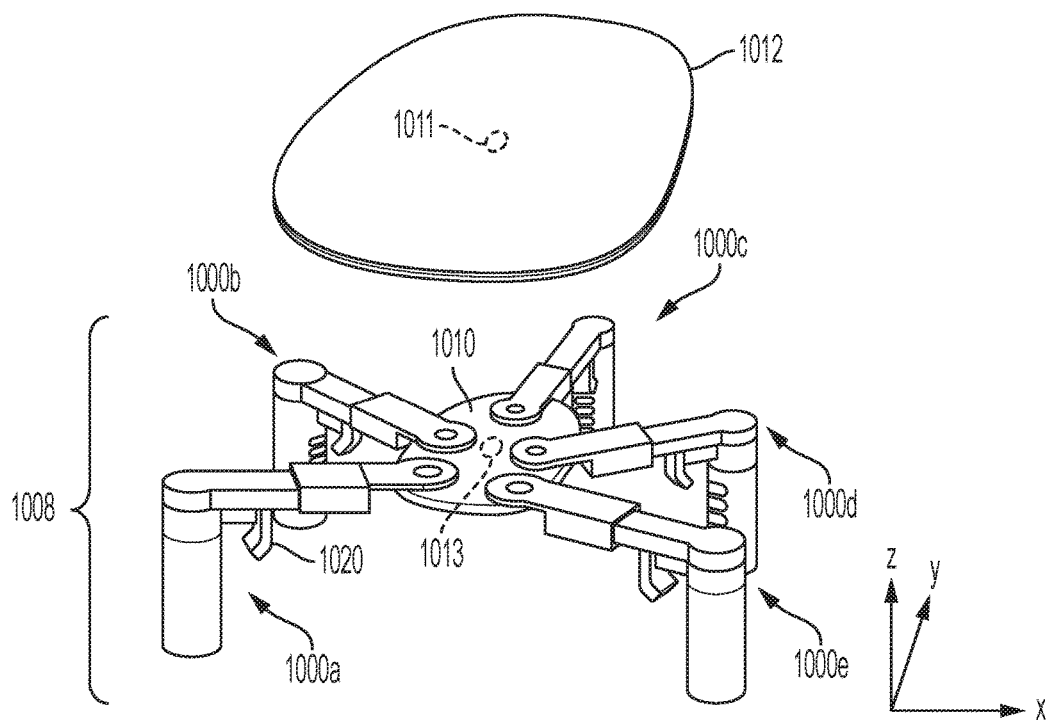
FIG. 10 is perspective view of second frame assembly, similar to the first frame assembly of FIG. 4 and a cover, according to aspects of the disclosure described herein.

FIG. 10 is perspective view of a second frame assembly 1008 (similar to the first frame assembly 408 of FIG. 4), and a cover 1012 (similar to the cover 412 of FIG. 4), according to aspects of the disclosure described herein. The second frame assembly 1008, includes five frames 1000a, 1000b, 1000c, 1000d, 1000e (each of the five frames is similar to the frame 300 of FIG. 3A). Each frame 1000a-1000e includes a dam securing member 1020 (similar to the dam securing member 320 of FIG. 3A). According to one example, a sixth fastener 1011 of the cover 1012 may couple to a seventh fastener 1013 of the base 1010 (similar to the base 410 of FIG. 4).

FIG. 11 depicts a resilient dam structure 1100 according to aspects described herein. The resilient dam structure 1100 may include a second example of a resilient dam 1104, a second example of a peripheral member 1106 on a circumference of the second example of the resilient dam 1104, and a plurality of attachment features 1102 distributed around the second example of the peripheral member 1106. The exemplary resilient dam structure 1100 is depicted as having rectangular cross-sections for the second example of the peripheral member 1106 and the plurality of attachment features 1102. This cross-section is exemplary and not limiting. Other cross-sectional shapes for the second example of the peripheral member 1106 and the plurality of attachment features 1102, such as round, square, or any cross-sectional shape as known to those in the art are within the scope of the disclosure.

In some embodiments, the resilient dam 404 including the peripheral member 406 of FIG. 4, as well as the resilient dam structure 1100 including the second example of the resilient dam 1104, the second example of the peripheral member 1106, and the plurality of attachment features 1102 of FIG. 11, may both be manufactured from a soft resilient plastic, latex, nitrile, rubber, rubber-like material, or similar materials as known in the art. In some embodiments the resilient dam 404 and the peripheral member 406 of the resilient dam 404 of FIG. 4, as well as the resilient dam structure 1100 including the second example of the resilient dam 1104, the second example of the peripheral member 1106, and plurality of attachment features 1102 of FIG. 11, may be formed as a unitary product or integrally formed (e.g., one piece made of the same material) together.

In some embodiments the resilient dam 404 and the peripheral member 406 of FIG. 4, as well as the resilient dam structure 1100 including the second example of the resilient dam 1104, the second example of the peripheral member 1106, and plurality of attachment features 1102 of FIG. 11, may be formed as two pieces. By way of example, the resilient dam 404 may formed separately from the peripheral member 406 and the two components may be mechanically joined prior to use. In a similar fashion with regard to the resilient dam structure 1100 of FIG. 11, the resilient dam 1104 may be separate from a unitary product or integrally formed combination of the peripheral member 1106 and plurality of attachment features 1102.

In some embodiments, the peripheral member 406 of FIG. 4, and a unitary product or integrally formed combination of the peripheral member 1106 and plurality of attachment features 1102 of FIG. 11, may each be comprised of two pieces that are cut in half along a plane parallel to the peripheral member 406 and peripheral member 1106, thus forming an upper piece/member and a lower piece/member. In such an example, the resilient dam 404 of FIG. 4 and the resilient dam 1104 of FIG. 11 may be trapped between the upper piece/member and a lower piece/member. Additionally, in this example, the resilient dam 404 of FIG. 4 and the resilient dam 1104 of FIG. 11 may be stretched over or across either the upper piece/member or the lower piece/member and then trapped between the two pieces/members. Additionally, it will be understood that recitation of peripheral member 406, peripheral member 1106, and plurality of attachment features 1102 contemplates these components as at least one of flexible, semi-flexible, or rigid.

Figure 12:
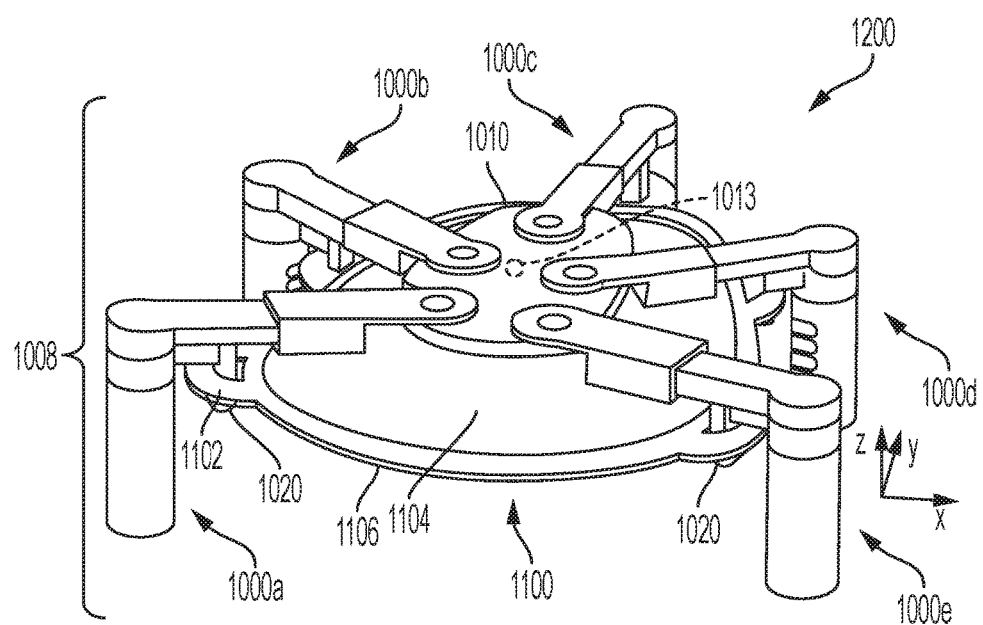
FIG. 12 is a perspective view of a frame assembly having a resilient dam structure of FIG. 11 coupled thereto, according to aspects of the disclosure described herein.

FIG. 12 is a perspective view of the second frame assembly 1008 having a resilient dam structure 1100 of FIG. 11, coupled thereto, according to aspects of the disclosure described herein. The illustrated configuration may be referred to as a common portion 1200 of a sleep apnea device 1300. The second frame assembly 1008 may include a plurality of frames 1000a, 1000b, 1000c, 1000d, 1000e and a base 1010. A location for a seventh fastener 1013 of the base 1010 is provided for reference.

As depicted in the example of FIG. 12, each of the plurality of attachment features 1102 of the resilient dam structure 1100 is formed as a loop or a D-shaped ring. These shapes are exemplary and not limiting. Other configurations and shapes for the plurality of attachment features 1102 as known to those in the art are within the scope of the disclosure. The exemplary loop or D-shaped ring of each of the plurality of attachment features 1102 hooks over onto a corresponding one of the plurality of dam securing members 1020. In this way the plurality of attachment features 1102 may be configured to be releasably secured by each of the dam securing members 1020.

FIG. 13 is a perspective view of a sleep apnea device 1300 in an operative state where a portion of a tongue 1308 is illustrated to illustrate the operational configuration of the sleep apnea device 1300. The sleep apnea device 1300 includes a bite block 1302 (similar to bite block 202 of FIG. 2), and a plurality of frames 1000*a*, 1000*b*, 1000*c*, 1000*d*, 1000*e* including a corresponding plurality of receiver 1304*a*-1304*e*. The sleep apnea device 1300 further includes a resilient dam structure 1100 and the base 1010 (similar to the base 410 of FIG. 4). By way of example, one clasp of a plurality of clasps 120 is illustrated in an operational configuration, where it is releasably secured to at least one of the lower teeth (e.g., 112, FIG. 1) (not shown) of a patient. The plurality of claps 120 may be releasably secured to the bite block 1302 by being configured to snap into or around receiving features (e.g., a depression, a raised rim or ridge) (not shown) of the bite block 202 or by being configured to grip (e.g., by friction or spring tension) the bite block 1302.

In the example of FIG. 13, the plurality of receivers are located on the left and right inner (lingual) side of the bite block 202 so as to be between the first and second lower (mandibular) molars, additional plurality of receivers (partially blocked from view by the tongue 1308) may be placed on the right and left inner (lingual) side of the bite block 1302 between the first and second lower (mandibular) bicuspids, and on the inner (lingual) side of the bite block 1302 between the third and fourth lower (mandibular) incisors. Other positioning is within the scope of the disclosure.

As previously noted in connection with FIG. 5, several advantages may be derived from physical arrangement of components in FIG. 13. The several advantages derived from physical arrangement of components in FIG. 13 are the same or similar to the several advantages derived from physical arrangement of components in FIG. 5 and will not be repeated for the sake of brevity.

Figure 14A:
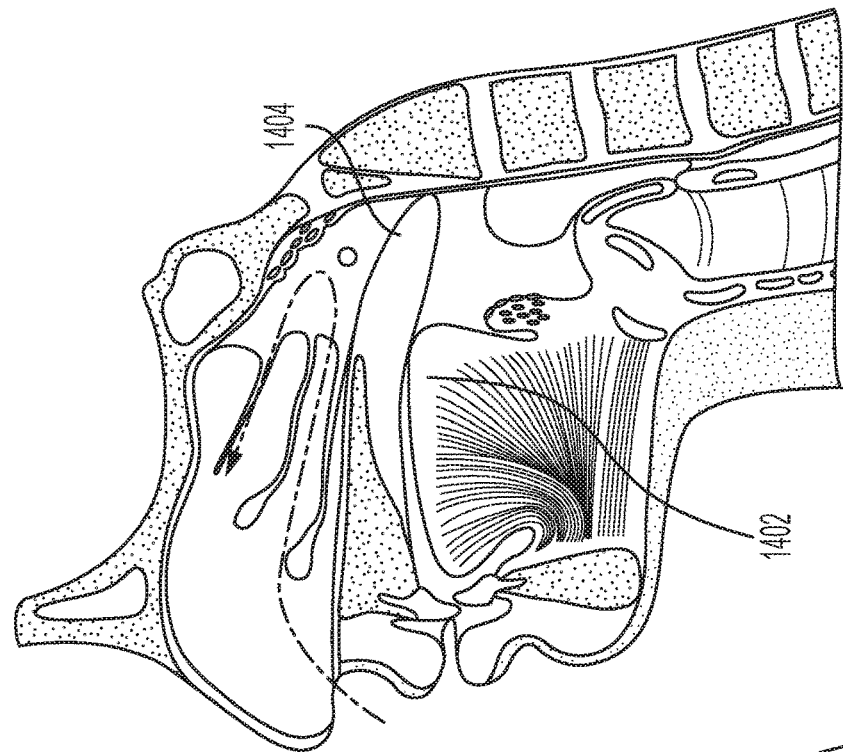
FIG. 14A is an anatomical cross-section of a head of a human patient showing the position of the tongue and soft palate when the patient is not swallowing.

FIG. 14A is an anatomical cross-section of a head of a human patient showing the position of the tongue 1402 and soft palate 1404 when the patient is not swallowing.

Figure 14B:
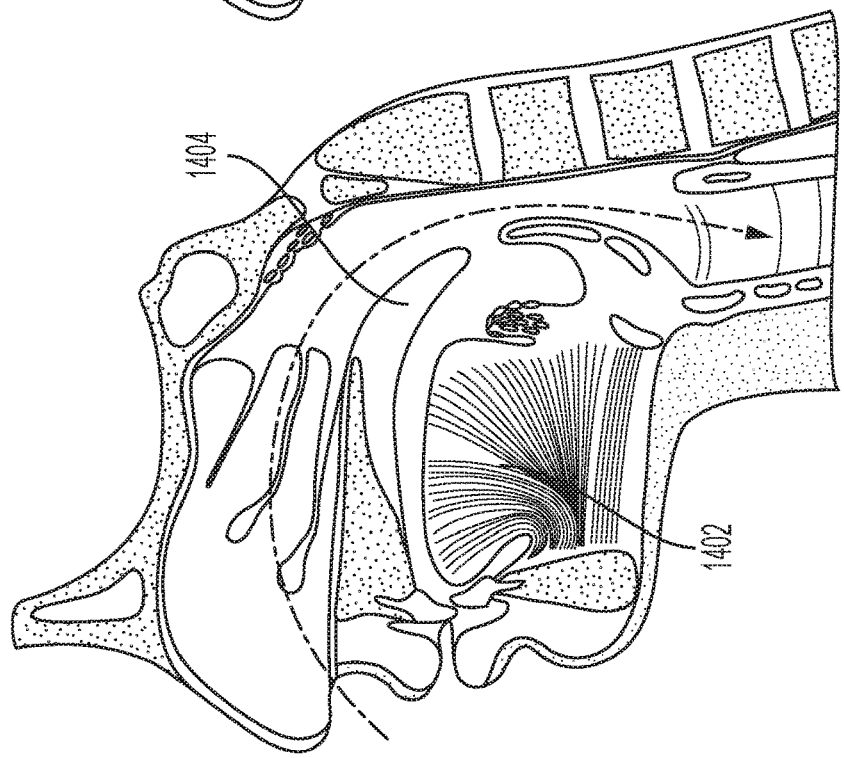
FIG. 14B is the anatomical cross-section of the head of the human patient of FIG. 14A showing the position of the tongue and soft palate when the patient is swallowing.

FIG. 14B is the anatomical cross-section of the head of the human patient of FIG. 14A showing the position of the tongue 1402 and soft palate 1404 when the patient is swallowing.

Figure 14C:
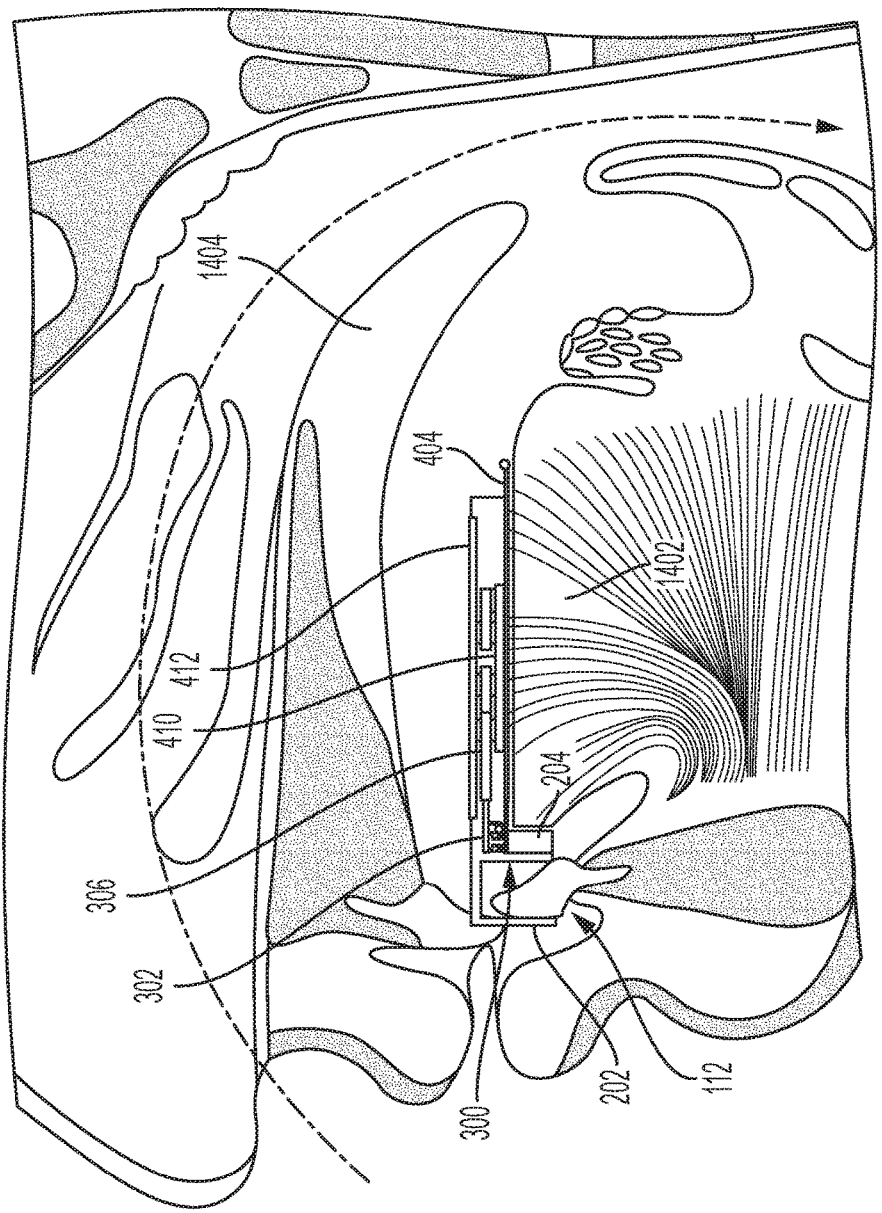
FIG. 14C is the anatomical cross-section of the head of the human patient of FIG. 14B showing the position of the tongue and soft palate when the patient is swallowing and a sleep apnea device, such as the sleep apnea device of FIG. 4, is fitted to the lower teeth of the patient, in accordance with aspects of the disclosure described herein.

FIG. 14C is the anatomical cross-section of the head of the human patient of FIG. 14B showing the position of the tongue 1402 and soft palate 1404 when the patient is swallowing and a sleep apnea device 400, such as the sleep apnea device 400 of FIG. 4 or 1300 of FIG. 13, is fitted to the lower teeth 112 of the patient, in accordance with aspects of the disclosure described herein.

The sleep apnea device 400 of FIG. 4 is used for explanatory and non-preferential reasons. A bite block 202, frame 300 (including receiver 204, transition piece 302, a base 410), and cover 412 are shown in cross-section. A resilient dam 404 and peripheral member 406 releasably secured by a dam securing member 320 are also shown in cross-section; however, the reference numbers and lead lines of the peripheral member 406 and dam securing member 320 are not present to avoid cluttering the drawing.

The tongue 1402 may be disposed to reside under the resilient dam 404. The tongue 1402 may rest against the lingual of the bite block 202 and the lingual of the plurality of receivers 204 (i.e., exteriors adjacent to the tongue 106), along the same surfaces that would generally touch the lower teeth 112 if the bite block 202 was not present. In some embodiments, the tongue 1402 may extend outward from under the edges of the resilient dam 404.

Figure 15:
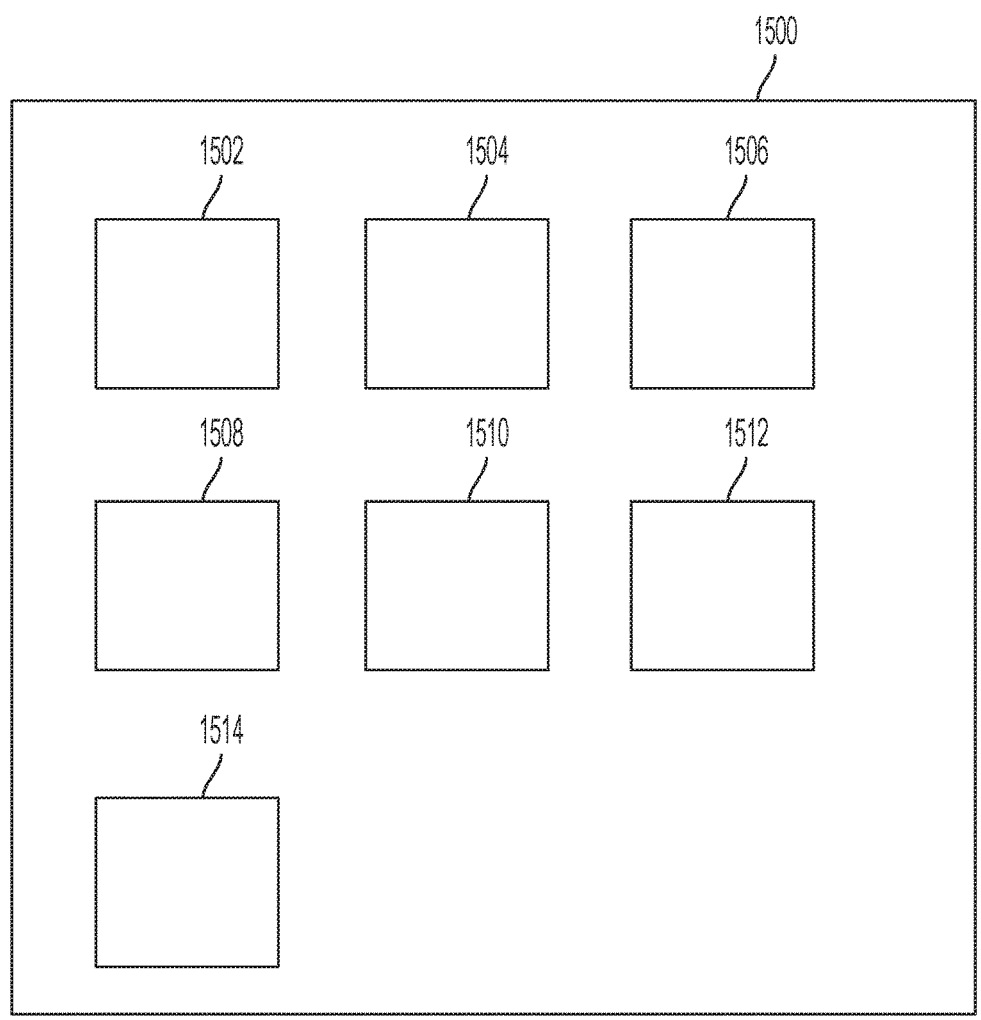
FIG. 15 is a block diagram representative of a kit configured for a sleep apnea patient, in accordance with aspects of the disclosure described herein.

FIG. 15 is a block diagram representative of a kit 1500 configured for a sleep apnea patient, in accordance with aspects of the disclosure described herein. The kit 1500 may include, for example: a bite block 1502 configured to be releasably secured to lower teeth of a lower jaw of the sleep apnea patient; a plurality of receivers 1504 configured to be coupled to a lingual surface of the bite block; a plurality of transition pieces and an associated plurality of base connectors 1506, corresponding to the plurality of receivers 1504, each transition piece of the plurality of transition pieces configured to have, a vertical portion configured to be coupled to a corresponding receiver of the plurality of receivers, a horizontal portion configured to extend from the vertical portion. According to some aspects, the horizontal portion may extend from the vertical portion, and, using various exemplary descriptions, may extend from the vertical portion toward an interior of an oral cavity of a patient, toward an interior of a mouth of a patient, toward a tongue of the patient. Each transition piece may also include a dam securing member. The kit 1500 may further include a base 1508 configured to have a plurality of second fasteners on a topside of the base 1508, each of the plurality of second fasteners configured to releasably couple to a corresponding first fastener on a bottom of a corresponding one of the plurality of base connectors. The kit 1500 may further include a resilient dam having a peripheral member (e.g., the resilient dam 404 and peripheral member 406 of FIG. 4) or a resilient dam structure (e.g., the resilient dam structure 1100 of FIG. 11), either one commonly referred to as the resilient dam 1510. The kit 1500 may further include a cover 1512 (similar to cover 412 of FIG. 4 or cover 1012 of FIG. 10). The kit 1500 may further include an instruction manual 1514 providing directions on assembly and/or use of the bite block 1502, the plurality of receivers 1504, the plurality of transition pieces and the associated plurality of base connectors 1506, the base 1508, the resilient dam 1510, and the cover 1512. When the bite block 1502 and the plurality of receivers 1504 are included with the kit 1500 as separate pieces (e.g., five receivers included with a bite block comprising six separate pieces), the kit optionally further includes at least one of: a bonding agent, an epoxy, a cement, or a glue, or the like as known to those in the art to facilitate coupling (e.g., attachment) of the plurality of receivers to a lingual surface of the bite block.

Although the disclosure has been described with respect to aspects of particular embodiments described herein, it should be realized that various changes and modifications may be made therein without departing from the spirit and scope of the disclosure.

One or more of the components and functions illustrated in the previous figures may be rearranged and/or combined into a single component or embodied in several components without departing from the invention. Additional elements or components may also be added without departing from the invention.

While certain exemplary embodiments have been described and shown in the accompanying drawings, it is to be understood that such embodiments are merely illustrative of and not restrictive on the broad invention, and that this invention is not be limited to the specific constructions and arrangements shown and described, since various other modifications may occur to those ordinarily skilled in the art.

Specific implementations shown and described are only examples and should not be construed as the only way to implement the present disclosure unless specified otherwise herein.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. In addition, unless stated otherwise, a set of elements may comprise one or more elements The word "exemplary" is used herein to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage or mode of operation. The term "coupled" is used herein to refer to the direct or indirect coupling between two objects. For example, if object A physically touches object B, and object B touches object C, then objects A and C may still be considered coupled to one another—even if they do not directly physically touch each other. Similarly, the term "coupled" is used herein with reference to features that may mechanically interact with each other in order to achieve a result. As used herein, the construct "A integral with B" means that A and B are one as a whole or comprise a single unitary body. As used herein, the term "A and/or B" means A, or B, or both (A and B). As used herein, the phrase "at least one of A or B" means A, or B, or both (A and B). The phrase "at least one of A, B, or C" means A, or B, or C, or "A and B," or "A and C," or "B and C," or "A and B," or "A and B and C." As used herein, the word "adjacent" may mean "next to" (including, alternatively, "next to and touching" and "next to and not touching") or proximate to. As used herein, words in the singular may include the plural, and words in the plural may include the singular.

What is claimed is:

1. A sleep apnea device, comprising:
   a bite block configured to be releasably secured to lower teeth of a patient;
   a plurality of receivers coupled to a lingual surface of the bite block;
   a plurality of transition pieces corresponding to the plurality of receivers, each transition piece of the plurality of transition pieces having:
      a vertical portion coupled to a corresponding receiver of the plurality of receivers,
      a horizontal portion configured to extend from the vertical portion, and
      a dam securing member fixed to one of the vertical portion, the horizontal portion, or both the vertical portion and the horizontal portion;
   a plurality of base connectors corresponding to the plurality of transition pieces, each of the plurality of base connectors coupled to the horizontal portion of a corresponding one of the plurality of transition pieces and configured to slide, with respect to the horizontal portion, toward and away from the vertical portion;
   a base coupled to the plurality of base connectors; and
   a resilient dam configured to be releasably secured by each dam securing member of the plurality of transition pieces.

2. The sleep apnea device of claim 1, wherein the bite block fits over the lower teeth and the sleep apnea device is configured to articulate with respect to upper teeth of an upper jaw of the patient.

3. The sleep apnea device of claim 1, wherein the plurality of receivers is coupled to the lingual surface of the bite block by being formed as one unit with the bite block.

4. The sleep apnea device of claim 1, wherein the plurality of receivers is coupled to the lingual surface of the bite block using at least one of: a bonding agent, an epoxy, a cement, or a glue.

5. The sleep apnea device of claim 1, wherein the vertical portion is coupled to the corresponding receiver by slidably engaging with a receiving portion of the corresponding receiver.

6. The sleep apnea device of claim 1, wherein a detent mechanism is formed by a first feature of the vertical portion of each transition piece engaged with a second feature of the corresponding receiver, and the detent mechanism is configured to provide a stepped vertical translation of each transition piece with respect to the corresponding receiver and to provide a predefined angular rotation of each transition piece with respect to the corresponding receiver.

7. The sleep apnea device of claim 6, wherein the predefined angular rotation is greater than or equal to about ±10 degrees and less than or equal to about ±45 degrees with respect to a central vertical axis of the corresponding receiver.

8. The sleep apnea device of claim 1, wherein the resilient dam is configured to allow a tongue of the patient slidably move against the resilient dam and prevent the tongue from sliding into an airway of the patient.

9. The sleep apnea device of claim 1, further comprising a cover coupled to the base.

10. The sleep apnea device of claim 9, wherein the cover has a top side and a bottom side and the cover is configured to be coupled to the base using a third fastener, fixed to or integral with the bottom side of the cover, that couples to a fourth fastener, fixed to or integral with a top side of the base.

11. The sleep apnea device of claim 9, wherein the cover has a top side and a bottom side and the cover is configured to be coupled to the base using a plurality of fasteners, fixed to or integral with the bottom side of the cover, that couple to a corresponding plurality of mating fasteners, each of the plurality of mating fasteners fixed to or integral with a top side of a corresponding base connector.

12. The sleep apnea device of claim 1, wherein in a coordinate system having an x-axis, a y-axis, and a z-axis, the base is configured to translate along the x-axis, translate along the y-axis, and rotate about the z-axis in response to movements of a tongue of the patient influencing a position of the base.

13. The sleep apnea device of claim 1, wherein in a coordinate system having an x-axis, a y-axis, and a z-axis, a translation of each of the plurality of transition pieces along the z-axis is selectively fixed in predetermined stepped increments.

14. The sleep apnea device of claim 1, wherein the resilient dam includes a peripheral member on a circumference of the resilient dam and the peripheral member is configured to be releasably secured by each dam securing member of the plurality of transition pieces.

15. The sleep apnea device of claim 1, wherein the resilient dam is included in a resilient dam structure comprising: the resilient dam, a peripheral member on a circumference of the resilient dam, and a plurality of attachment features distributed around the peripheral member, wherein the plurality of attachment features are configured to be releasably secured by each dam securing member of the plurality of transition pieces.

16. The sleep apnea device of claim 1, wherein the bite block is configured to be releasably secured to lower teeth of the patient with a plurality of clasps, each of the plurality of clasps having a first end configured to be secured to one or more of the lower teeth of the patient and a second end, distal to the first end, configured to be releasably secured to the bite block.

17. A kit for a sleep apnea device, comprising:
- a bite block configured to be releasably secured to lower teeth of a patient;
- a plurality of receivers configured to be coupled to a lingual surface of the bite block;
- a plurality of transition pieces corresponding to the plurality of receivers, each transition piece of the plurality of transition pieces having:
  - a vertical portion configured to be coupled to a corresponding receiver of the plurality of receivers,
  - a horizontal portion configured to extend from the vertical portion, and
  - a dam securing member fixed to one of the vertical portion, the horizontal portion, or both the vertical portion and the horizontal portion;
- a plurality of base connectors corresponding to the plurality of transition pieces, each of the plurality of base connectors configured to couple to the horizontal portion of a corresponding one of the plurality of transition pieces and configured to slide, with respect to the horizontal portion, toward and away from the vertical portion;
- a base configured to couple to the plurality of base connectors;
- a resilient dam configured to be releasably secured by each dam securing member of the plurality of transition pieces;
- a cover configured to couple to a third fastener on a top of each base connector of each of the plurality of transition pieces; and
- an instruction manual providing directions on assembly of the sleep apnea device comprised of the bite block, the plurality of receivers, the plurality of transition pieces, the base, and the resilient dam.

18. The kit of claim 17, wherein when the bite block and the plurality of receivers are included with the kit as separate pieces, the kit further includes at least one of: a bonding agent, an epoxy, a cement, or a glue to facilitate coupling of the plurality of receivers to a lingual surface of the bite block.

* * * * *